(12) United States Patent
Chen et al.

(10) Patent No.: US 8,796,508 B2
(45) Date of Patent: Aug. 5, 2014

(54) **MICROPROJECTILE BOMBARDMENT TRANSFORMATION OF *BRASSICA***

(75) Inventors: Wenpin Chen, Brampton (CA); Lomas Tulsieram, Mississauga (CA)

(73) Assignee: Pioneer Hi-Bred International, Inc., Johnston, IA (US)

(*) Notice: Subject to any disclaimer, the term of this patent is extended or adjusted under 35 U.S.C. 154(b) by 182 days.

(21) Appl. No.: 11/270,996

(22) Filed: Nov. 10, 2005

(65) Prior Publication Data

US 2007/0107077 A1    May 10, 2007

(51) Int. Cl.
*A01H 1/02*    (2006.01)
*A01H 5/10*    (2006.01)

(52) U.S. Cl.
USPC .......................... 800/293; 800/306; 800/268

(58) Field of Classification Search
None
See application file for complete search history.

(56) References Cited

U.S. PATENT DOCUMENTS

| | | | |
|---|---|---|---|
| 6,051,756 A | 4/2000 | Chen et al. | |
| 6,297,056 B1 | 10/2001 | Tulsieram et al. | |
| 6,307,123 B1 * | 10/2001 | Kriz et al. | 800/282 |
| 6,495,741 B1 | 12/2002 | Chen et al. | |
| 6,515,206 B1 | 2/2003 | Chaudhuri et al. | |
| 6,812,028 B1 * | 11/2004 | Kasha et al. | 435/430.1 |
| 7,297,838 B2 * | 11/2007 | Chen et al. | 800/294 |
| 2003/0093840 A1 | 5/2003 | Chen et al. | |
| 2003/0140382 A1 * | 7/2003 | Patell et al. | 800/293 |
| 2003/0200568 A1 | 10/2003 | Maliga et al. | |
| 2004/0045056 A1 | 3/2004 | Chen et al. | |
| 2004/0216191 A1 * | 10/2004 | Sandal et al. | 800/293 |

FOREIGN PATENT DOCUMENTS

WO    9943202 A1    9/1999

OTHER PUBLICATIONS

Vain et al. (Plant Cell Reports (1993) 12: 84-88.*
Chen, J.L., et al.; "A combined use of microprojectile bombardment and DNA inhibition enhances transformation frequency of canola (*Brassica napus* L.)."; Theor Appl Genet (1994) 88:187-192.
Fukuoka, H., et al.; "Direct gene delivery into isolated microspores of rapeseed (*Brassica napus* L.) and the production of fertile transgenic plants"; Plant Cell Rep (1998) 17:323-328.
Nehlin, L., et al.; "Transient B-gus and gfp gene expression and viability analysis of microprojectile bombarded microspores of *Brassica napus* L."; J Plant Physiol (2000) 156:175-183.
Poulsen, G.B., et al.; "Genetic transformation of *Brassica*"; Plant Breeding (1996) 115:206-225.
Souvre, A., et al.; "Transformation of rape (*Brassica napus* L.) through the haploid embryogenesis pathway"; ACTA Societutis Botanicorum Poloniae, Panstwowe Wydanietwo Naukowe, Warsaw, PL (1996) 65(112):194-195.

* cited by examiner

*Primary Examiner* — Brent T Page
*Assistant Examiner* — Jared Shapiro

(57) ABSTRACT

The invention relates to the genetic manipulation of plants, particularly plants of the genus *Brassica*. Methods are provided for producing transgenic *Brassica* plants involving the introduction of a DNA construct by microprojectile bombardment into pre-incubated microspores, microspore-derived embryos and microspore-derived hypocotyls. The methods find use in the development of improved agricultural varieties of *Brassica* plants through the incorporation of desirable agronomic traits.

13 Claims, No Drawings

MICROPROJECTILE BOMBARDMENT TRANSFORMATION OF *BRASSICA*

FIELD OF THE INVENTION

The field of the invention relates to the genetic engineering of plants, particularly methods for genetically transforming *Brassica* plants.

BACKGROUND OF THE INVENTION

*Brassica* species are used as a source of vegetable oil, animal feeds, vegetables and condiments. *Brassica* plants that are used for vegetable production include cabbage, cauliflower, broccoli, kale, kohlrabi, leaf mustard and rutabaga. Seeds of *B. hirta* are used to produce the popular American condiment, yellow mustard. However, on a world-wide basis, the most economically important use of *Brassica* species is for the production of seed-derived, vegetable oils. The predominant *Brassica* species grown for oil production is *B. napus*, followed by *B. juncea* and *B. rapa*. Seeds of *B. napus*, *B. juncea* and *B. rapa* are referred to as rapeseed. *Brassica* species that are grown primarily for oil production are often called oilseed rape. In North America, canola, a type of oilseed rape that has been selected for low levels of erucic acid and glucosinolates in seeds, is the predominant *Brassica* plant grown for the production of vegetable oil for human consumption. While low-erucic-acid rapeseed oils, such as canola oil, may be favored for human consumption, high-erucic-acid rapeseed oils are desirable for a variety of industrial applications including the production of cosmetics, lubricants, plasticizers and surfactants.

Because of the agricultural and industrial importance of plants from the genus *Brassica*, plant breeders are working to develop new varieties with improved agronomic characteristics. While traditional breeding approaches are important, significant improvements in cultivated *Brassica* varieties have been made recently through the introduction of recombinant DNA into the *Brassica* genome by genetic transformation methods. A number of genetically modified *Brassica* varieties have already reached farmers' fields in North America. Transgenic canola varieties, genetically modified for resistance to herbicides, have rapidly gained favor with agricultural producers across the canola-growing regions of the United States and Canada. The phenomenal success of the transgenic canola varieties in North America has led to acceleration in the development of new transgenic varieties of canola. Novel, recombinant DNA-based strategies for incorporating new traits, such as disease and insect resistance, modified seed oil composition and modified seed protein composition, are being developed for canola and other *Brassica* species. All of these strategies depend on genetic transformation methods to introduce the recombinant DNA into the genomes of *Brassica* plants.

Currently, the most favored methods for transforming *Brassica* species involve the use of *Agrobacterium*. While the *Agrobacterium*-based transformation methods provide a reliable means for introducing foreign DNA into plants, there are a number of disadvantages to methods of plant transformation that involve the use of *Agrobacterium*. First, an undesired consequence of all *Agrobacterium*-based methods is the introduction of at least one T-DNA border into the genome of the recipient plant. While the T-DNA border is an essential element of the genetic mechanism by which *Agrobacterium* transfers DNA to a plant cell, the T-DNA border is not essential for the expression of foreign genes in the recipient plant. Additionally, the accumulation of multiple T-DNA borders throughout the genome of a plant may have deleterious effects on the plant or its progeny. Second, the co-cultivation of plant tissues with *Agrobacterium* may slow the regeneration of a transformed plant from a transformed cell. After the co-cultivation phase, *Agrobacterium* must be eliminated from cultures of the plant tissues. High levels of bactericidal agents must be applied to the plant cultures to kill the *Agrobacterium*. While the levels of bactericidal agents applied to the cultures are generally not lethal to the plant tissues, the presence of the bactericidal agents in the cultures may negatively impact plant growth and thus, slow the regeneration of transformed plants. Third, prior to DNA transfer to a plant, natural genetic processes might occur in *Agrobacterium* such as genetic recombination and DNA rearrangements that may have undesired effects on the DNA fragment that is transferred to the plant. Such undesired effects may alter or eliminate the intended genetic function of the introduced DNA fragment.

Efficient *Brassica* transformation methods that do not involve the use of *Agrobacterium* are desired. U.S. Pat. No. 6,051,756, U.S. Pat. No. 6,495,741, US 2003/0093840 and US 2004/0045056 describe the transformation of seedling hypocotyls by particle bombardment. U.S. Pat. No. 6,297,056 describes the transformation of cotyledonary petioles. U.S. Pat. No. 6,515,206 and US 2003/0200568 describe the use of transformation of plastids in true leaves. Chen and Beversdorf *Theor. Appl. Genet.* 88: 187-192 (1994) describe a biolistic transformation procedure of microspore-derived hypocotyls involving DNA imbibition. Fukuoka et al. *Plant Cell Reports* 17: 323-328 (1998) describe biolistic transformation of fresh microspores. Finally, Nehlin et al., *Plant Physiol.* Vol. 156: 175-183 (2000) describe transient biolistic transformation of pre-incubated microspores, but no stable transgenics were reported.

To meet the increasing demands of agriculture in the world today, the pace of development of new transgenic varieties of canola and other *Brassica* species must be accelerated. Increasing the pace of *Brassica* variety development depends on the availability of reliable and efficient methods for the transformation and regeneration of transformed *Brassica* plants.

SUMMARY OF THE INVENTION

Methods are provided for producing transgenic *Brassica* plants. The methods comprise introducing DNA constructs by microprojectile bombardment. The introduced DNA constructs can encode proteins or can suppress endogenous genes. The methods find use in agriculture, particularly in the development of improved varieties of *Brassica* plants through the incorporation of desirable agronomic traits. The methods involve introducing a DNA construct by microprojectile bombardment into a *Brassica* cell that is capable of regenerating into a stably transformed *Brassica* plant and regenerating such a *Brassica* plant from the cell.

An aspect of the invention is to provide a method of producing a transformed *Brassica* cell by particle bombardment, comprising: (a) culturing a pre-incubated microspore-derived explant comprising a cell under a condition of plasmolysis for a period of about half an hour to about 4 hours prior to bombardment; (b) introducing a DNA construct by microprojectile bombardment into an exposed cell on a surface of the pre-incubated microspore-derived explant, wherein the explant is under the condition of plasmolysis; and (c) continuing to culture the bombarded pre-incubated microspore-derived explant under the condition of plasmolysis for a period of about 4 hours to about 20 hours, to produce a transformed Brassica cell. A pre-incubated microspore-derived explant is a microspore or any tissue derived from the microspore (for example a microspore-derived embryo or a microspore-derived hypocotyl) that has been cultured for a period of time of between 1 day and 30 days prior to bombardment. The condition of plasmolysis can be selected from the group consisting of (a) culturing the explant on osmotic medium and (b) culturing the explant on wetted filter paper. The explant can be a pre-incubated microspore, a pre-incubated microspore-derived embryo, or a pre-incubated microspore-derived hypocotyl. The method can further comprise the steps of regenerating a transformed plant from the transformed cell, comprising: (a) culturing said microspore-derived explant on a regeneration medium to produce a regenerated embryo or tissue; and (b) regenerating a stably transformed Brassica plant from said embryo or tissue An aspect of the present invention is to provide a method for producing a stably transformed Brassica plant, comprising: (a) introducing a DNA construct by microprojectile bombardment into a pre-incubated explant, which may be a microspore, or a microspore-derived embryo or portion of a microspore-derived embryo; (b) culturing the pre-incubated explant to produce an embryo or tissue; and (c) regenerating a stably transformed Brassica plant from the embryo or tissue. In step (a), a pre-incubated microspore can be produced by culturing a microspore in a culture medium for a period of about two to ten days prior to bombardment. The period can be from about four to eight days, or from seven to eight days. The method can further comprise a step of inducing plasmolysis of the pre-incubated microspore prior to, during and after bombardment. For example, plasmolysis can be induced by (a) culturing the pre-incubated microspore on osmotic medium prior to, during and after bombardment, or (b) culturing the pre-incubated microspores on wetted filter paper prior to, during and after bombardment. The osmotic medium can comprise between about 17 and 19% sucrose and between about 0.8 and 1.6% Phytagel™ agar (w/v). The pre-incubated microspore can be cultured on osmotic medium for about between half an hour and four hours prior to bombardment and for about between four hours and twenty hours after bombardment.

The method can further comprise a selection step after bombardment comprising culturing the bombarded pre-incubated microspore on a medium comprising a selection agent against a gene encoded by the DNA construct. For example, the selection agent can be selected from the group consisting of kanamycin, G418 and glyphosate. The concentration of G418 can be between about 5 and 10 mg/l. The concentration of glyphosate in the medium can be between about 0.1 mM and 0.2 mM. The method may further comprise a step of orientating the pre-incubated microspore during bombardment so that a surface of the microspore is exposed during the bombardment. The method may further comprise a step of collecting the pre-incubated microspore such that it is viable and embryogenic prior to bombardment. The step of collecting the pre-incubated microspore can be a filtration step or a step of Percoll® gradient centrifugation (Percoll® concentration is 35-45%). The filtration step can be done using a sieve having a pore size of about 15 to 48 μm.

In step (a), of the method, the microprojectile bombardment can be conducted using bombardment factors comprising about 12.5 ng to 5 μg of said DNA construct, about 15 μg to 100 μg gold particles per shot at the size of 0.4 micron to 0.6 micron, about 2.5 M $CaCl_2$ and a 650 to 900 psi rupture disk. The step of regenerating a stably transformed plant can comprise culturing the bombarded pre-incubated microspore on a first liquid selection medium for a first period of time, a second liquid selection medium for a second period of time, and then transferring the resistant embryo or tissue derived from the pre-incubated microspore to solid medium for a third period of time. The first period of time can be about 7 days and the pre-incubated microspore can be cultured in darkness. The pre-incubated microspore, or tissue or embryo derived from the pre-incubated microspore, can be cultured in the second liquid selection medium for approximately 14 days in dim light of approximately 240 foot candles or 2,583 Lux. The second liquid medium can be liquid NLN-6.5S and further comprise growth regulators. The growth regulators in the second liquid selection medium can comprise 0.5 mg/L NAA and 0.05 mg/l BAP. Further, the first, the second, or both the first and the second liquid selection media can comprise G418 or glyphosate. Further, the solid medium may comprise growth regulators to induce regeneration, and optionally further comprise a selection agent against a gene encoded by the DNA construct. The solid medium can be MMW medium with indoleacetic acid (IAA), thidiazuron (TDZ) and silver nitrate ($AgNO_3$). The solid medium can further comprise a selection agent against a gene encoded by the DNA construct. The method can further comprise use of a chromosome doubling agent to produce a doubled haploid transgenic plant. The doubling agent can be administered within one day after bombardment and can be administered for approximately 7 days.

Where the bombarded explant of the invention is a microspore-derived embryo, the method may comprise: (a) culturing a microspore-derived embryo on osmotic medium for a period of about half an hour to about 4 hours prior to bombardment; (b) introducing a DNA construct by microprojectile bombardment into an exposed surface of the microspore-derived embryo on osmotic medium; (c) continuing to culture the bombarded microspore-derived embryo on osmotic medium for a period of about 4 hours to about 20 hours; (d) culturing said bombarded microspore-derived embryo on regeneration media to produce a regenerated embryo or tissue; and (e) regenerating a stably transformed Brassica plant from the regenerated embryo or tissue. The microspore-derived embryo can be between about 11 and 20 days old. The microspore-derived embryo can be between about 11 and 14 days old. The method can further comprise the step of collecting the embryo using a pipette and transferring the embryo onto filter paper prior to step (a). Step (d) can comprise culturing the embryo on liquid medium for a first period of time and then on solid medium for a second period of time. The first period of time can be about 7 to 14 days. The method can further comprise an optional step of excising a hypocotyl from the regenerated embryo and culturing the hypocotyl on regeneration media. Additionally, the method can further comprise a step of selecting for a transformed embryo comprising culturing the embryo on media supplemented with a selection agent against a gene encoded by the DNA construct. The method can comprise use of a chromosome doubling agent to produce a double haploid transgenic plant.

Where the bombarded explant of the invention is a portion of a microspore-derived embryo, the method may comprise: (a) culturing a hypocotyl excised from a microspore-derived embryo on osmotic medium for a period of about half an hour to about 4 hours prior to bombardment; (b) introducing a DNA construct by microprojectile bombardment into an exposed surface of the microspore-derived hypocotyl on osmotic medium; (c) continuing to culture the bombarded microspore-derived hypocotyl on osmotic medium for a period of about 4 hours to 20 hours; (d) culturing said microspore-derived hypocotyl on a regeneration medium to produce regenerated embryos or tissues; and (e) regenerating a stably transformed *Brassica* plant from said embryo or tissue. The microspore-derived hypocotyl can be excised from a microspore-derived embryo of between about 21 and 26 days. The method can further comprise a step of culturing the microspore-derived hypocotyl on a cell division induction medium comprising plant growth regulators for between about 1 to 20 hours prior to bombardment. Step (d) can comprise culturing the embryo on a first solid medium for a first period of time and then on a second solid medium for a second period of time. The first solid medium can comprise plant growth regulators for bud induction. The second solid medium can be free of plant growth regulators or comprises plant growth regulators for shoot formation. The method can further comprise a step of selecting a transformed embryo or tissue comprising culturing the embryo or tissue on media supplemented with a selection agent against a gene encoded by the DNA construct. The method can further comprise use of a chromosome doubling agent to produce a doubled haploid transgenic plant.

Another aspect of the invention is to provide a *Brassica* cell or a stably transformed *Brassica* plant produced by any one of the methods described above. The plant or cell can be selected from *Brassica napus*, *Brassica rapa*, *Brassica juncea*, *Brassica oleracea*, *Brassica carinata* and *Brassica nigra*. Progeny of the plant and cell are also provided.

DETAILED DESCRIPTION OF THE INVENTION

The invention is drawn to methods for transforming *Brassica* plants. The methods find use in agriculture in the development of transgenic crop plants with improved agronomic characteristics. The methods find particular use in introducing desirable traits into a *Brassica* plant. Such new traits may be, for example, resistance to an herbicide, resistance to pathogens and insects, modified seed oil composition and the like. The methods involve introducing a DNA construct into the genome of a cell of a *Brassica* plant and regenerating a stably transformed plant from the cell.

A number of terms used herein are defined and clarified in the following section.

By "*Brassica* cell" is intended a cell from a *Brassica* plant or a cell that is produced by in vitro culture methods and is descended from a cell from a *Brassica* plant.

By "somatic embryo" is intended an embryo that develops from a somatic cell. The developmental process by which a somatic embryo develops from a cell is known as "somatic embryogenesis." Such a "somatic embryo" is distinct from a "zygotic embryo" which develops from a zygote.

By "microspore-derived embryo" is intended an embryo that develops from a microspore. Because it develops from a germ cell, such a "microspore-derived embryo" is distinct from both somatic and zygotic embryos which develop from somatic cells and zygotes, respectively.

By "microspore-derived hypocotyl" is intended a hypocotyl of an embryo that develops from a microspore.

By "adventitious" is intended an organ or other structure of a plant that does not originate in the usual location on the plant body. For example, a shoot that originated from a hypocotyl of a microspore-derived embryo is an "adventitious shoot."

By "canola" is intended a *Brassica* plant or oil from a *Brassica* plant wherein the oil must contain less than 2% erucic acid and the solid component of the seed must contain less than 30 micromoles of any one or any mixture of 3-butenyl glucosinolate, 4-pentenyl glucosinolate, 2-hydroxy-3-butenyl glucosinolate, and 2-hydroxy-4-pentenyl glucosinolate per gram of air-dry, oil free solid.

By "organogenesis" is intended the developmental process wherein a cell or group of cells gives rise to an organ such as, for example, a shoot, a bud or a root.

By "chromosome doubling" is intended that each of the chromosomes in a cell is duplicated resulting in a doubling of the number of chromosomes in the cell.

By "ploidy" is intended the number of complete sets of chromosomes in the nucleus of a cell. A "haploid" cell has one set of chromosomes, and a "diploid" cell has two sets.

By "effective amount" is intended an amount of an agent, compound or plant growth regulator that is capable of causing the desired effect on an organism. It is recognized that an "effective amount" may vary depending on factors, such as, for example, the organism, the target tissue of the organism, the method of administration, temperature, light, relative humidity and the like. Further, it is recognized that an "effective amount" of a particular agent may be determined by administering a range of amounts of the agent to an organism and then determining which amount or amounts cause the desired effect.

By "pre-incubated microspore-derived explant" is intended a microspore or any tissue derived from the microspore (for example a microspore-derived embryo or a microspore-derived hypocotyl) that has been cultured for a period of time of between about 1 day and 30 days prior to bombardment. For example, a pre-incubated microspore may be cultured for about two to ten days from the time of isolation of the microspore from a donor plant. For example, a pre-incubated microspore-derived embryo may be cultured for a period of about 11 days to 20 days from the time of isolation of the microspore from a donor plant. For example, a pre-incubated microspore-derived hypocotyl may be cultured for a period of about 21 to 26 days from the time of isolation of the microspore from a donor plant.

By "progeny" is intended descendents of a particular cell or plant which comprise at least a portion of the transgene inserted at the locus of the genome of the T0 plant cell. For example, progeny can be seeds developed on a plant and plants derived from such seeds. For example, progeny of a plant include seeds formed on T0, T1, T2 and subsequent generation plants, and plants derived from such seeds. Progeny also includes seeds formed by cross pollination using pollen of a T0, T1, T2, T3, etc. plant. For example, the progeny can be the result of selfing, outcrossing or backcrossing. The progeny can also include asexually propagated plants or cells derived from T0, T1, T2, etc plants or cells that include at least a portion of the transgene inserted at the locus of the genome in the T0 plant cell. For example, plants produced via cuttings, tissue culture, microspore culture, etc. that comprise at least a portion of the original transgene inserted at the locus of the genome of the T0 plant cell are also considered progeny.

Methods are provided for transforming a *Brassica* plant. The methods involve transforming a *Brassica* cell with a DNA construct by microprojectile bombardment. The methods further involve regenerating the transformed cell into a transformed *Brassica* plant. Such a transformed *Brassica* plant possesses at least one copy of the DNA construct, or portion thereof, incorporated into its genome. The transformed *Brassica* plants of the invention may be stably transformed *Brassica* plants. Such transformed *Brassica* plants are capable of producing at least one offspring that possesses at least one copy of the DNA construct of the invention, or portion thereof, stably incorporated within its genome.

Cells of the present invention may originate from (1) pre-incubated microspores, (2) microspore-derived embryos or (3) microspore-derived hypocotyls. It is recognized that the cells of these tissues are most likely haploid. The cells may be diploid if the cells undergo spontaneous chromosome doubling, or if the cells are subjected to chromosome doubling agents. Transformation of haploid cells is advantageous because the resulting chromosome doubled transgenic plant is homozygous.

A DNA construct of interest is introduced into the cell by microprojectile bombardment. Microprojectile bombardment is also known by other terms, including particle bombardment, microparticle bombardment, ballistic particle acceleration and biolistic transformation. Generally, such methods involve applying to or coating the surface of microprojectiles with the DNA construct of interest, and then delivering the DNA-coated microprojectiles to the target tissue at a velocity sufficient to allow the particles to pass through cell walls and membranes and thus, enter plant cells. See, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental. Methods, ed. Gamborg and Phillips (Springer-Verlag, Berlin); and McCabe et al. (1988) *Biotechnology* 6:923-926.

The methods of the invention do not depend on a particular DNA construct. Any DNA construct that may be introduced into a cell by microprojectile bombardment may be employed in the methods of the invention. DNA constructs of the invention may comprise at least one nucleotide sequence of interest operably linked to a promoter that drives expression in a plant cell. DNA constructs may comprise a selectable marker gene and at least one additional nucleotide sequence of interest operably linked to a promoter that drives expression in a plant cell. Additionally, DNA constructs may comprise a selectable marker gene and at least one additional nucleotide sequence that is capable of conferring a desired trait on a *Brassica* plant.

The methods of the present invention additionally comprise regenerating the transformed cell of the invention into a stably transformed *Brassica* plant. Regeneration of the transformed plant involves culturing the transformed cell under conditions that result in the growth and development of the transformed cell into a transformed plant. The transformed cell or descendents thereof may develop into a transformed embryo, particularly a transformed microspore-derived embryo or somatic embryo which then develops into a transformed plant. Alternatively, the transformed cell and descendents thereof may develop into a transformed organ, such as, for example, an adventitious shoot. It is recognized that regenerating a transformed *Brassica* plant from a transformed cell via an adventitious shoot may additionally involve the formation of callus before adventitious shoot formation. Such an adventitious shoot may be used to produce the stably transformed *Brassica* plant by methods known in the art. Such methods generally involve culturing an adventitious shoot in a medium and environment which favors the formation of adventitious roots on the adventitious shoot.

Methods for rooting adventitious shoots are known in the art. The methods of the present invention do not depend on a particular method for rooting transformed *Brassica* shoots. Any method known in the art for rooting adventitious shoots may be employed in the methods of the present invention. Generally, rooting adventitious shoots will involve incubating shoots, for a period of time, on a medium that contains an effective amount of an auxin, such as, for example, indolebutyric acid, to induce root formation. See, for example, Moloney et al. (1989) *Plant Cell Reports* 8:238-242 and Radke et al. (1992) *Plant Cell Reports* 11:499-505. Rooted shoots may then be removed from culture, transferred to soil or potting medium and subjected to environmental conditions that favour growth, maturation and seed production.

It is recognized that the transformed embryos, transformed adventitious organs, and transformed plants of the invention may be chimeric. That is, such transformed embryos, organs and plants may be comprised of both transformed and non-transformed cells, or may be comprised of two or more differentially transformed cells. It is further recognized that such chimeric plants may give rise to progeny plants that comprise a DNA construct of interest, or portion thereof, stably incorporated into the genomes of all of their somatic and germ line cells.

The methods of the invention involve the transformation of cells from *Brassica* plants. The cells may be haploid cells. While haploid cells generally do not give rise to diploid plants, it is recognized that occasionally a haploid cell may spontaneously give rise to a diploid cell that is capable of developing into a fertile plant. If necessary, chromosome-doubling agents may be employed in the methods of the invention to increase the ploidy of a haploid cell two fold. That is, a haploid cell becomes a diploid cell. Such a diploid cell may give rise to a fertile, stably transformed *Brassica* plant. The methods of the present invention do not depend on a particular genetic mechanism of chromosome doubling. It is likely, however, that chromosome doubling results from chromosome duplication as would occur for example, during mitosis, but in the absence of cytokinesis.

Induced chromosome doubling of the invention involves administering an effective amount of a chromosome-doubling agent to a cell, preferably a haploid cell. Any agent that is known to increase the ploidy of cells may be employed in the methods of the invention. Chromosome-doubling agents include, but are not limited to, trifluralin, colchicine, oryzalin, amiprophosmethyl and pronamide. Depending on the desired outcome, a chromosome-doubling agent may be administered to a tissue, or a cell thereof, before, after, or both before and after, introducing a DNA construct into a cell by microprojectile bombardment. In certain methods of the invention, an effective amount of a chromosome-doubling agent is administered after bombardment.

The plants regenerated from transformed *Brassica* cells are referred to as the T0 generation or T0 plants. The seeds produced by various sexual crosses of T0 generation plants are referred to as T1 progeny or T1 generations. When T1 seeds are germinated, the resulting plants are also referred to as T1 generation. Seeds produced on the T1 plant or from crosses using T1 pollen, are referred to as T2 seeds, which give rise to T2 plants. Seeds produced on the T2 plant or from crosses using T2 pollen, are referred to as T3 seeds. T3 seeds give rise to T3 plants. Accordingly, the generations progress through T4, T5, T6, etc. The seeds and plants of the T1, T2, T3, T4, etc. can be analyzed to ensure successful transmission of the transgene. Various sexual crosses are possible. For example, the plants can be selfed, outcrossed or backcrossed. Alternatively, the transgenic plants (T0, T1, T2, etc) can be propagated asexually, for example by cloning, tissue culture, cuttings, microspore culture, etc. as is known to those skilled in the art.

In a first embodiment of the invention, methods are provided for transforming *Brassica* pre-incubated microspores and regenerating stably transformed plants therefrom.

The methods of the first embodiment involve bombarding pre-incubated microspores with microprojectiles coated with a DNA construct of interest. Microspores are isolated by methods that are known to those skilled in the art. For example, see Fukuoka et al. (1996) *Plant Physiol.* 111:39-47;

Keller et al. (1987) *Proc. 7th Int. Rapeseed Congr.* (Plant Breeding and Acclimatization Institute, Poznan, Poland) pp. 152-157, Swanson et al. (1987) *Plant Cell Reports* 6: 94-97 and Baillie et al. (1992) *Plant Cell Reports* 11: 234-237. The microspores are haploid. The microspores may be isolated and cultured in a medium with a high level of sucrose, for example 17% sucrose, for 2 to 3 days. The high level of sucrose is recommended to ensure the integrity of the microspores immediately after isolation. Further, high osmotic stress would have a positive effect on embryogenesis induction (Maraschin et al., 2005 *J Exp Bot* 56:1711-1726 and Prem et al. 2005 *In Vitro Cell. Dev. Biol.*—Plant 41:266-273). The microspores are then cultured for 4 to 8 days in medium containing a reduced level of sucrose, for example in the range of 10% sucrose to promote microspore division. Accordingly, a pre-incubation period of 2 to 10 days is within the scope of the invention.

After the pre-incubation period, the pre-incubated microspores are collected in a manner to enrich for viable and embryogenic microspores. This can be done, for example, by using a Nitex™ sieve of 15 to 48 µm in pore size. The pore size may be between 15 and 25 µm. The embryogenic microspores can also be enriched by Percoll® gradient centrifugation (Touraev 1996 *Sex Plant Reprod* 9: 209-215). Percoll® concentration is between 35 to 45%. The Nitex™ sieve holding the pre-incubated microspores is then placed on an osmotic treatment medium prior to bombardment, during bombardment and for a period of time after bombardment. The osmotic treatment induces slight plasmolysis of the microspores to ensure they will not burst due to the bombardment procedure. During bombardment, a surface of the microspores may be exposed to the path of the bombarding particles coated with DNA to facilitate entry of the particles and also to prevent any sudden influx of medium (i.e. the surface of the microspores that is exposed is not embedded in the medium). The osmotic treatment facilitates this. For example, the pre-incubated microspores may be subjected to the osmotic treatment for 1 to 2 hours prior to bombardment, during the bombardment, and for 1 to 24 hours after bombardment. For example, the osmotic treatment may comprise placing the pre-incubated microspores on medium containing between 0.8 to 1.6% Phytagel™ or agar, between 17 and 19% sucrose and 1 g/l MES (2-[N-Morpholino]ethanesulfonic acid). The osmotic treatment can also be done by placing microspores (optionally on sieves) in a petri dish (3.5 cm in diameter) prior to bombardment, during the bombardment and after the bombardment. A piece of filter paper (3.2 cm in diameter) wet with NLN-13S medium is placed in the petri dish to prevent microspore dehydration.

Following bombardment, the microspores and sieve can be cultured in medium containing a doubling agent and a high level of sucrose, for example 13% sucrose, for about 7 days.

If the DNA construct of interest comprises a selectable marker gene, the bombarded pre-incubated microspores may be transferred to medium containing an appropriate selective agent for that particular selectable marker gene. Such a transfer may occur immediately after bombardment or after a period of time. For example, the transfer may occur between 0 and about 30 days after bombardment.

During the selection stage, the pre-incubated microspores may be sub-cultured in selection NLN medium, which may contain a reduced sucrose content, for example 6.5% and growth regulators, for example cytokinins and auxins. Selection may be conducted in the light. The pre-incubated microspores may then be monitored for the appearance of transformed embryos and/or adventitious shoots. Such transformed embryos and/or adventitious shoots may then be cultured in shoot regeneration medium that may contain MS or B5 components and further, may also contain selection agents (for example, kanamycin or glyphosate) with or without plant growth regulators. The regenerated shoots are rooted in B5 medium containing 0.1 mg/l $GA_3$.

In a second embodiment of the invention, methods are provided for transforming cells from microspore-derived embryos with microprojectiles coated with a DNA construct of interest. Methods are known in the art for producing embryos from *Brassica* microspores. See Fukuoka et al (1996) *Plant Physiol.* 111:39-47 and Keller et al. (1987) *Proc. 7th Int Rapeseed Congr.* (Plant Breeding and Acclimatization Institute, Poznan, Poland) pp. 152-157. Like the microspores themselves, the cells comprising such microspore-derived embryos are haploid. In the methods of the invention, whole microspore-derived embryos are bombarded with DNA-coated microprojectiles. The microspore-derived embryos may be greater than 10 days old and approximately greater than 1.5 mm in size. The microspore-derived embryos can be between 11 and 20 days old. The embryos may be globular or heart shaped. The embryos are placed on osmotic medium prior to, during and after bombardment for the same reasons as discussed above. At least one surface of the embryos should be exposed to the path of the bombarded particles (i.e. not in the medium) during bombardment to facilitate entry of the particle and to avoid any sudden influx of medium into the cell. For example, the embryos may be subjected to the osmotic treatment for approximately 4 hours prior to bombardment and for approximately 20 hours (for example, overnight) after bombardment. The osmotic treatment may comprise, for example, a medium containing 17 to 19% sucrose and 1.5% agar, and acts to prevent the cells of the embryos from bursting during and after bombardment. Alternatively, the osmotic treatment may comprise placing the embryos on a petri dish having a wet filter paper. The embryos are then transferred to regeneration medium. The regeneration media may include, but are not limited to, B5 media, MS-based media (MS salts with organics, 2% (w/v) sucrose, 0.6% (w/v) Sigma agar, pH 5.8). Embryo-derived hypocotyls may be excised and cultured in selection medium to induce transgenic shoots. Typically, a microspore-derived embryo gives rise to a single or a few adventitious shoots as a result of growth from the apical meristem or hypocotyl area. Methods of the second and third embodiments can involve adventitious shoot regeneration of the microspore-derived embryos and microspore-derived hypocotyls. Such methods find use in increasing the number of transformed plants recovered from a transformation attempt.

Adventitious shoot regeneration involves the formation of multiple shoots arising from a microspore-derived embryo. Thus, a single microspore-derived embryo can yield multiple transformed shoots from a transformation. Typically, all of the transformed shoots that arise from a single microspore-derived embryo are thought to be an independent transformant. That is, each transformed shoot is derived from an independently transformed cell and thus, is genetically distinct. For the purposes of this investigation, however, all multiple events from each embryo were combined.

Methods of adventitious shoot regeneration are known in the art. While the methods of the present invention do not depend on a particular method of adventitious shoot regeneration, the methods may involve subjecting the microspore-derived embryos to an effective amount of cytokinin to induce adventitious shoots. Adventitious shoot regeneration may be accomplished within less than about 30 days after administering a cytokinin to the microspore-derived embryos. Adventitious shoot regeneration may be accomplished within less than about 10 days after administering the cytokinin. The methods of secondary regeneration of the present invention may additionally involve subjecting the microspore-derived embryos to an effective amount of an auxin. In exemplary methods, an effective amount of a cytokinin is administered, with or without an effective amount of an auxin, to the microspore-derived embryos following bombardment to induce adventitious shoot regeneration.

If the DNA construct utilized in methods of the second embodiment comprises a selectable marker gene, selection may be applied immediately after bombardment or after a period of time of less than 2 day to about 30 days. Selection may be applied by subjecting the microspore-derived embryos to an effective amount of an appropriate selective agent for the selectable marker gene of the DNA construct of interest. An effective amount of the selective agent may be added to the medium on which the microspore-derived embryo is cultured. The selective agent may be administered alone or in combination with one or more other compounds such as a chromosome-doubling agent or a plant growth regulator.

In a third embodiment of the invention, methods are provided for particle bombardment of microspore-derived hypocotyls. As discussed above, microspores are isolated and cultured as is known to those skilled in the art. Approximately 21 days after culture, when the embryos are generally torpedo shaped, the culture medium is diluted with fresh culture medium and the microspores are allowed to culture for approximately 5 more days. The majority of the embryos are generally at the cotyledon stage after 26 days in culture. Hypocotyl sections from the embryos are excised and cultured for a period of time on medium supplemented with plant growth regulators to induce cell division. For example, the excised hypocotyls may be cultured overnight on MMW+4 mg/l BAP+0.25 mg/l NAA.

Prior to bombardment, during bombardment and after bombardment, the excised hypocotyls are subjected to osmotic treatment as described above. In addition, a surface of the hypocotyls in direct line with the bombardment route is exposed to the path of the bombarding particle (i.e. the surface of the hypocotyls that is in the direct line with the bombardment route is not embedded in the medium) to facilitate entry of the particle coated with DNA and to avoid any sudden influx of medium. The osmotic medium may comprise 17 to 19% sucrose, 1.5% agar and 1 g/l MES. The hypocotyls may be cultured on the osmotic medium for 4 hours prior to bombardment and overnight after bombardment. After osmotic treatment, the hypocotyls may be transferred to bud induction medium (for example, MMW+4 mg/l BAP+25-100 mg/l KAN). A bud can be an immature shoot, leaf, embryo or flower. Hypocotyls comprising adventitious buds may then be transferred to shoot regeneration medium (for example, MMW without hormones, or MMW+0.2 mg/l BAP). A selection agent may be added to any of the media after bombardment.

Additionally, the methods of the first, second, and third embodiments may comprise administering an effective amount of a chromosome doubling agent to the culture medium before, or optionally after, bombardment. Adding a chromosome doubling agent is not necessary in all cases, because the rate of spontaneous doubling can be high, especially in the embodiments employing microspore-derived embryos and microspore-derived hypocotyls. Such chromosome-doubling agents and methods of use are known to those skilled in the art and were discussed above.

The methods of the present invention involve the use of plant growth regulators such as, for example, auxins sand cytokinins. The plant growth regulators of the invention include, but are not limited to, both free and conjugated forms of naturally occurring plant growth regulators. Additionally, the plant growth regulators of the invention encompass synthetic analogues and precursors of such naturally occurring plant growth regulators.

Naturally occurring and synthetic analogues of auxins include, but are not limited to, indoleacetic acid (IAA), 3-indolebutyric acid (IBA), a-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), (4-chloro-2-methylphenoxy) acetic acid (MCPA), 4-(4-chloro-2-methylphenoxy) butanoic acid (MCPB), mecoprop, dicloprop, quinclorac, picloram, triclopyr, clopyralid, fluroxypyr and dicamba.

Naturally occurring and synthetic analogues of cytokinins include, but are not limited to, kinetin, thidiazuron (TDZ), zeatin, zeatin riboside, zeatin riboside phosphate, dihydrozeatin, isopentyl adenine and 6-benzyladenine (BAP).

The methods of the present invention may include use of G418 disulfate salt (Gibco™), also sold as Geneticin™ from Fluka as a selection agent or glyphosate as a selection agent. After bombardment of pre-incubated microspores, selection may be done in liquid medium in dark first and then under low light intensity (for example, approximately 240 foot-candles or 2,583 lux). However, other selection agents, as is known to those skilled in the art, can be used. For example, kanamycin (Beck et al. (1982) *Gene* 19:327-336; Mazodier et al. (1985) *Nucleic Acids Res.* 13:195-205), and other herbicides, like Basta™ and Chlorsulfuron™.

Stable transgenic plants may be confirmed by polymerase chain reaction (PCR) analysis and Southern blot hybridization analysis.

The use of the term "DNA constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein.

Thus, the DNA constructs of the present invention encompass all nucleotide constructs which can be employed in the methods of the present invention for transforming *Brassica* plants including, but not limited to, those comprised of deoxyribonucleotides, ribonucleotides and combinations thereof. Such deoxyribonucleotides and ribonucleotides include both naturally occurring molecules and synthetic analogues. The DNA constructs of the invention also encompass all forms of nucleotide constructs including, but not limited to, single-stranded forms, double-stranded forms, hairpins, stem-and-loop structures and the like.

Furthermore, it is recognized that the methods of the invention may employ a DNA construct that is capable of directing, in a transformed plant, the expression of at least one protein, or at least one RNA, such as, for example, an rRNA, a tRNA or an antisense RNA that is complementary to at least a portion of an mRNA. Typically such a DNA construct is comprised of a coding sequence for a protein or an RNA operably linked to 5' and 3' transcriptional regulatory regions. Alternatively, it is also recognized that the methods of the invention may employ a DNA construct that is not capable of directing, in a transformed plant, the expression of a protein or RNA.

In addition, it is recognized that methods of the present invention do not depend on the incorporation of the entire DNA construct into the genome, only that the genome of the *Brassica* plant is altered as a result of the introduction of the DNA construct into a *Brassica* cell. For example, alterations to the genome include additions, deletions and substitution of nucleotides in the genome. While the methods of the present invention do not depend on additions, deletions, or substitutions of any particular number of nucleotides, it is recognized that such additions, deletions or substitutions comprise at least one nucleotide.

The DNA constructs of the invention also encompass nucleotide constructs, that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731, 181; 5,756,325; 5,760,012; 5,795,972; and 5,871,984. See also, WO 98/49350, WO 99/07865, WO 99/25821 and Beetham et al. (1999) *Proc. Natl. Acad. Sci. USA* 96:8774-8778.

Additionally, the term "DNA-coated microprojectiles" used herein is not intended to limit the methods of the present invention to microprojectiles coated with DNA. Rather, the term "DNA-coated microprojectiles" as used herein encompasses microprojectiles coated with any one or more of the DNA constructs of the invention as described supra.

The DNA constructs of the invention may be comprised of expression cassettes for expression in the *Brassica* plant of interest. The expression cassette may include 5' and 3' regulatory sequences operably linked to a gene of interest. By "operably linked" is intended a functional linkage between a regulatory sequence and a second sequence, wherein the regulatory sequence affects initiation and mediation of transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the gene of interest sequence to be under the transcriptional regulation of the regulatory regions. The expression cassette may additionally contain selectable marker genes.

The expression cassette may include in the 5'-3' direction of transcription, a transcriptional and translational initiation region, a gene of interest and a transcriptional and translational termination region functional in plants. The transcriptional initiation region, the promoter, may be native (or analogous) or foreign (or heterologous) to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the gene of interest using heterologous promoters, the native promoter sequences may be used. Such constructs would change expression levels of the gene of the interest in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. In addition, the gene can undergo gene shuffling to enhance expression. For example, the glyphosate acetyl transferase gene used in the examples underwent gene shuffling (Castle et al. (2004) *Science* 304:1151-1154 and WO 02/36782A2).

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein et al. (1989) *PNAS USA* 86:6126-6130); potyvirus leaders, for example, TEV leader (Tobacco Etch Virus) (Allison et al. (1986) *Virology* 154: 9-20); MDMV leader (Maize Dwarf Mosaic Virus); Virology 154: 9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in Molecular Biology of RNA, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in *Brassica* plants.

Such constitutive promoters include, for example, the core promoter of the Rsyn7 (U.S. Pat. No. 6,072,050); the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-25 632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), SCP (WO 97/47756A1, WO 99/438380); H2b (Rasco-Gaunt et al. (2003) *Plant Cell Rep.* 21:569-576); SCP1 (U.S. Pat. No. 6,677,503 B1) and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced expression of the gene of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hanson et al. (1997) *Mol. Gen Genet.* 254(3):337-343; Russell et al. (1997) *Transgenic Res.* 6(2):157-168; Rinehart et al. (1996) Plant PhysioL 112 (3):1331-1341; Van Camp et al. (1996) *Plant Physiol.* 112(2):525-535; Canevascini et al. (1996) *Plant Physiol* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mot Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

"Seed-preferred" promoters include both "seed development" promoters (those promoters preferentially active during seed development such as promoters of seed storage proteins) as well as "seed-germinating" promoters (those promoters preferentially active during seed germination). See Thompson et al. (1989) *BioEssays* 10:108. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see U.S. Pat. No. 6,225,529). For dicots, seed-specific promoters include, but are not limited to, bean β-phaseolin (Chandrasekharan et al., 2003 *Plant J.* 33: 853-866), napin, β-conglycinin (Chamberland et al. 1992 *Plant Mol. Biol.* 19: 937-949), soybean lectin, cruciferin, and the like.

Various changes in phenotype are of interest including modifying the fatty acid composition in a plant, altering the amino acid content of a plant, altering a plant's pathogen defense mechanism, enhancing tolerance to abiotic stress, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes or nucleotide sequences of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered by methods of the invention in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,990,389, 5,885,801, 5,885,802, and 5,703,409. Another example is lysine and/or sulfur rich seed protein encoded by the soybean 2S albumin described in U.S. Pat. No. 5,850,801, and the chymotrypsin inhibitor from barley, described in Williamson et al. (1987) *Bur. J. Biochem.* 165: 99-106

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, WO 98/20133. Other proteins include methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Ill.), pp. 497-502); corn (Pedersen et al. (1986) *J. Biol. Chem.* 261:6279; Kirihara et al. (1988) *Gene* 71:359); and rice (Musumura et al. (1989) *Plant Mol. Biol.* 12:123). Other agronomically important genes encode latex, Floury 2, growth factors, seed storage factors, and transcription factors.

Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825; Ahman et al. 2000 WO0001223); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Genes conferring resistance to *Sclerotinia* have been introduced into sunflower and *Brassica* (U.S. Pat. No. 6,441,275 B1). An endochitinase gene under a constitutive promoter was introduced into canola (*Brassica napus* var. *oleifera*) inbred line. Progeny from the transformed plants were challenged using three different fungal pathogens (*Cylindrosporium concentricum, Phoma lingam, Sclerotinia sclerotiorum*) in field trials. The plants exhibited an increased tolerance to disease as compared with the nontransgenic parental plants (Grison et al. (1996) *Nature Biotechnology* 14: 643-646). Additional disease resistance genes are discussed in Stewart and Broadway, 2005 (US6927322); Salmeron et al. 2003 (US6528702) and Chye and Zhao 2002 (US20030097682).

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or Basta® (e.g., the bar gene), or other such genes known in the art. The ALS-gene mutants encode resistance to the herbicide chlorsulfuron (Swanson et al (1989) *Theor Appl Genet* 78:525-530, EP0257993 B1). The glyphosate acetyl transferase (GAT) gene confers resistance to glyphosate (Castle et al. (2004) *Science* 304:1151-1154).

Sterility genes can also be encoded in an expression cassette and provide an alternative to physical emasculation. Examples of genes used in such ways include male tissue-preferred genes and genes with male sterility phenotypes such as avidin and streptavidin, described in U.S. Pat. No. 5,962,769 (Albertsen et al., 1999) and Barnase (Block and Debrouwer (1993) *Planta* 189: 218-225) Other genes include kinases and those encoding compounds toxic to either male or female gametophytic development.

The quality of seed is reflected in traits such as levels and types of oils, saturated and unsaturated, quality and quantity of essential amino acids, and levels of cellulose. For example, U.S. Pat. Nos. 5,990,389, 5,885,801, 5,885,802, and 5,703,409, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as R-Ketothiolase, PHBase (polyhydroxybutyrate synthase), and acetoacetyl-CoA reductase (see Schubert et aL (1988) *J. Bacleriol.* 170:5837-5847) facilitate expression of polyhydroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

It is recognized that a DNA construct of the present invention may comprise an antisense construction complementary to at least a portion of a messenger RNA (mRNA) of a gene of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% or more sequence identity to the complementary sequences may be used. Furthermore, portions of the antisense nucleotides may be used to disrupt the expression of the target gene. Generally, sequences of at least 50 nucleotides, 100 nucleotides, 200 nucleotides, or greater may be used. Typically, such antisense constructions will be operably linked to a promoter that drives expression in a plant.

The DNA constructs of the invention may also be employed in sense suppression methods to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, for example, greater than about 65%, 85% or 95% sequence identity. See, U.S. Pat. Nos. 5,283,184 and 5,034,323.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NPTII), and hygromycin phosphotransferase (HPT). Genes conferring resistance to herbicidal compounds may also be used, such as glyphosate acetyl transferase, glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) Handbook of Experimental Pharmacology, Vol. 78 (Springer-Verlag, Berlin); Gill et al. (1988) *Nature* 334:721-724.

In addition, the expression cassette may comprise a screenable marker gene, for example the gene encoding β-glucuronidase (GUS) (Jefferson et al. (1986) *Proc. Natl. Acad. Sci. USA* 83:8447-8451; Jefferson et al. (1987) *EMBO J.* 6:3901-3907) or the gene encoding the green fluorescent protein (GFP) (Chalfie et al. (1994) *Science* 263: 802-805).

The above list of selectable marker genes and screenable marker genes is not meant to be limiting. Any selectable and/or screenable marker gene can be used in the present invention.

*Brassica* plants of the invention include, but are not limited to, *Brassica carnata* (Ethiopian mustard), *Brassica juncea* (leaf mustard), *Brassica napus* (rape), *Brassica napus* var. *rapifera* (Swedish turnip), *Brassica nigra* (black mustard), *Brassica oleracea*, *Brassica oleracea* var. *acephala* (kale), *Brassica oleracea* var. *alboglabra* (Chinese kale), *Brassica oleracea* var. *hotrytis* (cauliflower, heading broccoli), *Brassica oleracea* var. *capitata* (cabbage), *Brassica oleracea* var. *gemmifera* (Brussel sprouts), *Brassica oleracea* var. *gongylodes* (Kohlrabi), *Brassica rapa* (field mustard; also known as *Brassica* campestris), *Brassica rapa* subsp. *chinensis* (bokchoy), and *Brassica rapa* subsp. *pekinensis* (Chinese cabbage).

In certain embodiments of the invention, the *Brassica* plants of the invention are oilseed *Brassica* plants. Such oilseed Brassica plants are used for oil production and include but are not limited to, Brassica juncea, Brassica napus and Brassica rapa. The Brassica plants may be canola plants. Such canola plants are selections of oilseed Brassica plants (Brassica rapa, Brassica napus and Brassica juncea) that contain low levels of both erucic acid and glucosinolates in their seeds. Canola oil must contain less than 2% erucic acid and the solid component of the seed must contain less than 30 micromoles of any one or any mixture of 3-butenyl glucosinolate, 4-pentenyl glucosinolate, 2-hydroxy-3 butenyl glucosinolate, and 2-hydroxy-4-pentenyl glucosinolate per gram of air-dry, oil free solid. The seeds of such canola plants are favored for the extraction of edible oils.

EXPERIMENTAL

Microspore-Derived Embryos

Experiments 1 to 2 describe the work done using microspore-derived embryos as the target tissue. Microspores were isolated as is known to those skilled in the art, for example, see Swanson et al. 1987 and cultured in NLN medium (see Section entitled "Media Recipes" for components of all media used in this invention) for approximately 11 to 14 days. However, the microspore-derived embryos can be cultured for between 11 to 20 days. The embryos were produced from the microspores and were detectable with the naked eye. The size of the microspore-derived embryos was generally smaller than 1 mm and the embryos were globular or heart shaped.

The microspore-derived embryos were collected to enrich for viable embryos. For example, this may be done using a pipette and transferring the embryos to a filter paper or membrane, for example Gelman™ membrane (Prod. No. 60110). The filter paper or membrane can have a 0.8 µm pore size. The embryos and membrane were cultured on osmotic medium for example, the medium may contain 17 to 19% sucrose+0.8 to 1% agar+1 g/l MES, pH 6.0. The embryos were subjected to the osmotic treatment before, during and after bombardment. For example, the embryos were subjected to the osmotic treatment for 4 hours prior to bombardment. The DNA construct used in bombardments was PHP18644. PHP18644, and other vectors used are described in the Table 9. The bombardment was done as is known to those skilled in the art, using approximately 10 ng to 5 µg of DNA per preparation, 15 µg to 300 µg of gold particles of approximately 0.4-1.0 micron per shot, $CaCl_2$ at 0.5M to 2.5M and a rupture disk of 650, 900 or 1100 psi. After bombardment, the embryos were cultured on the osmotic medium for 4 hours to 20 hours (approximately overnight) and then transferred to liquid NLN medium. The bombarded embryos were subsequently cultured for 7 to 14 days. The bombarded embryos or hypocotyls excised from the embryos at age 3 to 4 weeks were transferred from liquid NLN medium to solid selection medium MMW+IAA+TDZ+K25-50 (embryos) or MMW+BAP+K25-50 (hypocotyls) for bud induction. The resistant regenerated buds were excised and cultured on MMW-H+K50-100 for plant regeneration.

Experiment 1

Effect of Various Rupture Disks on GUS Transient Expression Using Microspore-Derived Embryos The objective was to screen different rupture disks to determine those that would result in the highest transformation efficiency.

Part A: Fourteen day old microspore-derived embryos were pre-incubated for 4 hours on osmotic medium containing 17% sucrose, 1 g/l MES and 10 g/l agar with pH 6.0. The microspore-derived embryos were bombarded with PHP18644 precipitated on gold particles (100 µg/shot). The bombarded embryos were cultured for 4 hours after bombardment on the osmotic medium containing 17% sucrose, 1 g/l MES and 10 g/l agar with pH 6.0 and then cultured in NLN medium. Rupture disks of 450 psi, 650 psi and 900 psi were tested.

Transient transformation efficiency was determined by analyzing the bombarded embryos using the GUS assay, as is known to those skilled in the art. Table 1 shows the results of the GUS assay. Rupture disk 900 psi produced the greatest number of cells expressing GUS in this experiment.

TABLE 1

Effect of cultivar and rupture disk on GUS transient expression using microspore-derived embryos

| Rep # | Rupture disk | # of bombarded embryos | GUS dots/embryos |
|---|---|---|---|
| Rep 1 | 450 psi | 200 | 4 |
|  | 650 psi | 193 | 5.7 |
|  | 900 psi | 207 | 2.9 |
| Rep 2 | 450 psi | 107 | 7.5 |
|  | 650 psi | 54 | 20.4 |
|  | 900 psi | 51 | 31.4 |
| Rep 3 | 450 psi | 39 | 69.2 |
|  | 650 psi | 39 | 76.9 |
|  | 900 psi | 51 | 80.4 |

Part B: The construct used was PHP18644. Bombarded small embryos were cultured in NLN-13S for 2-3 weeks. The embryos or excised hypocotyls from the embryos were cultured in bud regeneration medium MMW+IAA+TDZ+kanamycin (50 mg/l) (embryos) or MMW+BAP+Kanamycin (50 mg/l) (for hypocotyls).

Table 2 shows the results of resistant shoot formation using different rupture disk strengths. In part B of the experiment, no significant difference was found using the 650 psi, 900 psi or 1100 psi rupture disks. The 650 and 900 psi rupture disks were easiest to use because less time was required to achieve the pressure to rupture the disks. Accordingly, the 650 psi and 900 psi rupture disks were used in later experiments. Table 2 also shows that excising hypocotyl segments from the bombarded embryos results in resistant shoot formation.

TABLE 2

Effect of rupture disk on resistant bud production from bombarded microspore-derived embryos

| Rep # | Rupture disks (psi) | # hypocotyls or # Embryos | Resistant buds (%) |
|---|---|---|---|
| Rep 1 | 650 | 300 (E) | 0 (0.0) |
|  | 900 | 350 (E) | 0 (0.0) |
|  | 1100 | 450 (E) | 1 (0.2) |
| Rep 2 | 650 | 150 (H) | 2 (1.3) |
|  | 1100 | 150 (H) | 0 (0.0) |
| Rep 3 | 650 | 400 (E) | 0 (0.0) |
|  | 900 | 400 (E) | 1 (0.3) |
|  | 1100 | 400 (E) | 0 (0.0) |
| Rep 4 | 650 | 850 (H) | 5 (0.6) |
|  | 900 | 525 (H) | 3 (0.6) |
|  | 1100 | 775 (H) | 3 (0.4) |

Experiment 2

Resistant Shoot Production from Bombarded Microspore-Derived Embryos in Solid Kanamycin Selection Medium and Confirmation of the Kanamycin Resistant Plants by Polymerase Chain Reaction (PCR) Analysis The objective was to demonstrate that kanamycin resistant plants were produced from bombarded microspore-derived embryos. The construct used was PHP18644 and the cultivar was 46A65. Kanamycin resistant shoots were produced by bombardment of microspore-derived embryos. The shoots were regenerated into kanamycin resistant plants. The kanamycin resistant plants were analyzed using the REDExtract-N-AMP™ plant PCR kit from Sigma as is known to those skilled in the art. DNA was extracted from 14 kanamycin resistant plants and analyzed by PCR for the nptII gene. Table 3 indicates that the nptII gene was found in 12 of the 14 plants. Accordingly, stable transgenic plants were obtained by bombarding microspore-derived embryos.

TABLE 3

Detection of nptII gene in kanamycin resistant plants regenerated from bombarded microspore-derived embryos

| Rep | # Events | PCR-nptII positive |
|---|---|---|
| Rep 1 | 9 | 7 |
| Rep 2 | 5 | 5 |
| Total | 14 | 12 |

Microspore-Derived Hypocotyls:

Experiments 3 to 7 describe work done using microspore-derived hypocotyls. Microspores were isolated as is known to those skilled in the art and cultured in NLN medium for 21 to 28 days (Swanson et al., 1987). Hypocotyls were excised from the embryos produced from the microspores when the embryos were approximately 3-5 mm in size.

Microspores of cultivar 46A65 were cultured in NLN medium for approximately 21 days. On the 21st day, the NLN medium was changed and diluted (1:20) with fresh NLN medium and the embryos were cultured for 5 more days. The hypocotyls were excised from the embryos and preconditioned overnight on MMW+BAP (4 mg/l)+NAA (0.25 mg/l). The hypocotyls were transferred to osmotic medium (for example, 17% sucrose+1% agar+1 g/l MES, pH 6.0) for 4 hours and then bombarded. The DNA construct used in bombardments was PHP18644. After bombardment, the hypocotyls were cultured on the osmotic medium for approximately between 4 and 20 hours (for example, overnight). The bombarded hypocotyls were then cultured on MMW+BAP (4 mg/l)+kanamycin (25-50 mg/l) for bud induction. Regenerated buds were cultured on MMW+kanamycin (50-100 mg/l) or MMW+BAP (0.2 mg/l)+kanamycin (50-100 mg/l) for plant regeneration.

The following experiments were done to test the effect of sucrose concentration, amount of gold particle used and the effect of rupture disk on transformation frequency.

Experiment 3

Effect of Sucrose Concentration in Osmotic Medium on Transient GUS Expression on Microspore-Derived Hypocotyls The objective was to find the appropriate concentration of sucrose in the osmotic medium (sucrose+1% agar+1 g/l MES, pH 6.0) in order to produce the highest transformation efficiency.

Sucrose concentrations of 15, 17, 19 and 21% were tested as shown in Table 4. The results indicated that using 19% sucrose produced the greatest number of transiently transformed cells.

TABLE 4

Effect of sucrose concentration in osmotic medium on transient GUS expression in microspore-derived hypocotyls

| Sucrose (%) | # hypocotyls | # with GUS | # total spots | # spots/ hypocotyls |
|---|---|---|---|---|
| 15 | 24 | 23 | 236 | 9.8 |
| 17 | 24 | 23 | 242 | 10.1 |
| 19 | 24 | 23 | 475 | 19.8 |
| 21 | 24 | 24 | 400 | 16.7 |

Experiment 4

Determining the Effect of the Amount of Gold Used per Shot on Transient GUS Expression in Microspore-Derived Hypocotyls The objective was to determine the optimal amount of gold particles per bombardment.

The construct used was PHP18644. Table 5 shows the results using 100, 200 and 300 µg of gold per shot. The results were not consistent in three experiments. 100 µg gold particles per shot were used in the remainder of the experiments.

TABLE 5

Effect of the amount of gold particle per bombardment on GUS transient expression using microspore-derived hypocotyls

| Rep # | Gold amount/shot (ug) | # hypocotyls | # with GUS spots | Spots/per hypocotyls |
|---|---|---|---|---|
| 1 | 100 | 32 | 1 | 0.1 |
|   | 200 | 32 | 4 | 0.5 |
|   | 300 | 33 | 4 | 1.3 |
| 2 | 100 | 24 | 24 | 39.6 |
|   | 200 | 24 | 24 | 29.6 |
|   | 300 | 25 | 25 | 35.4 |
| 3 | 100 | 24 | 21 | 20.1 |
|   | 200 | 24 | 24 | 26.8 |
|   | 300 | 24 | 24 | 40.1 |

Experiment 5

Effect of Rupture Disks on GUS Transient Expression on Microspore-Derived Hypocotyls The objective was to determine which of four rupture disk strengths tested produced the greatest number of cells expressing GUS.

The construct used was PHP18644. Table 6 shows the results of GUS transient expression using a rupture disk strength of 450 psi, 650 psi, 900 psi or 1100 psi. Results indicate that using rupture disks 650 psi and 900 psi produced the highest number of cells transiently expressing GUS.

TABLE 6

Effect of rupture disk strength on GUS transient expression using microspore-derived hypocotyls

| Rep | Rupture disks | # hypocotyls | # with GUS spots | # GUS spots/hypocotyls |
|---|---|---|---|---|
| 1 | 450 | 24 | 23 | 19.5 |
|   | 650 | 24 | 24 | 48.3 |
|   | 900 | 25 | 24 | 37.4 |
|   | 1100 | 24 | 22 | 27.5 |
| 2 | 650 | 24 | 24 | 60.7 |
|   | 900 | 25 | 25 | 60.5 |
|   | 1100 | 25 | 25 | 49.4 |

Experiment 6

Second Experiment to Determine the Effect of Rupture Disk on Resistant Bud Production Using Microspore-Derived Hypocotyls The objective was to screen rupture disks to determine those that produced the greatest number of resistant buds on 50 mg/l kanamycin.

The construct used was PHP18644. Table 7 shows the results using rupture disks of 450 psi, 650 psi and 900 psi. No significant difference was found between rupture disks 450 psi, 650 psi and 900 psi in this experiment.

TABLE 7

Effect of rupture disk strength on the production of kanamycin resistant shoots using microspore-derived hypocotyls as the bombardment tissue

| Rep # | Rupture disks | # hypocotyls | # with green buds |
|---|---|---|---|
| 1 | 450 psi | 375 | 6 (1.6%) |
|   | 650 psi | 525 | 8 (1.5%) |
|   | 900 psi | 300 | 5 (1.7%) |
| 2 | 450 psi | 200 | 1 (0.5%) |
|   | 650 psi | 225 | 1 (0.4%) |
|   | 900 psi | 100 | 1 (1.0%) |
| 3 | 450 psi | 300 | 2 (0.7%) |
|   | 650 psi | 300 | 1 (0.3%) |
|   | 900 psi | 300 | 2 (0.7%) |
| 4 | 450 psi | 300 | 0 (0.0%) |
|   | 650 psi | 250 | 0 (0.0%) |
|   | 900 psi | 300 | 3 (1.0%) |
| 5 | 450 psi | 150 | 1 (0.7%) |
|   | 650 psi | 275 | 5 (1.8%) |
|   | 900 psi | 200 | 3 (1.5%) |
| 6 | 450 psi | 125 | 0 (0.0%) |
|   | 650 psi | 75 | 0 (0.0%) |
|   | 900 psi | 25 | 1 (4.0%) |

Experiment 7

Results of the GUS Assay on the Kanamycin Resistant Plants

The objective was to confirm the transgenic status of the kanamycin resistant plants by GUS analysis. Table 8 shows that seven kanamycin resistant plants were analyzed by GUS assay. Six plants were positive. This confirms that stable transgenic plants were produced by bombarding microspore-derived hytocotyls.

TABLE 8

Confirmation of transgenic status of kanamycin resistant plants from microspore-derived hypocotyls by GUS analysis

| Rep # | Resistant Plants | GUS Positive Plants |
|---|---|---|
| Rep 1 | 2 | 2 |
| Rep 2 | 3 | 2 |
| Rep 3 | 1 | 1 |
| Rep 4 | 1 | 1 |

Pre-Incubated Microspores:

Experiments 8 to 17 describe the work done using pre-incubated microspores. The microspores were cultured in NLN-17S/10S for 2-10 days. Optimally, the microspores are cultured for 5-7 days. Embryos could not be detected with the naked eye. The embryogenic microspores were collected so that they remain viable and embryogenic with a Nitex™ sieve (15-36 um in pore size) or Percoll® (35-45%) gradient centrifugation.

Pre-incubated microspores were used as bombarded materials. Any *Brassica* line that is capable of regenerating by microspore culture can be used. The microspores were cultured for 1-3 days in NLN-17S at 31.5° C., and then in NLN-10S for 4-5 days at 25° C. The constructs used in the bombardments were PHP18644, PHP21965, PHP22024, PHP22021, and PHP23560 (see Table 9). The constructs can be the full plasmid or the expression cassette only. For example, PHP22024 can be either the expression cassette or the full plasmid. The pre-incubated microspores were filtrated with sieves of pore size of 15 μm to 36 μm. The collected microspores were used for bombardment. The microspores were loaded on a sieve 15 μm or 20 μm on two layers of filter-paper and dried for less than one minute. The microspores and sieves were transferred to osmotic medium that contained B5 components, 1 g/l MES and 0.8-1.6% gelrite, 15-21% sucrose (pH 6.0). The microspores were treated for at least one hour on the osmotic medium before bombardment. The pre-incubated microspores were bombarded with 12.5 ng to 5 μg DNA per preparation, 15-100 μg Au particles per shot, 2.5 M CaCl2, and 650-900 psi rupture disk. During bombardment a surface of the pre-incubated microspores was exposed to the path of the bombarded particles coated with DNA (i.e. the surface was not embedded in the medium). The bombarded microspores were cultured at least four hours in the osmotic medium after bombardment. One to two sieves holding the microspores were cultured in 5 ml of NLN-13S with or without glyphosate per plate for approximately 7 days in the dark. After the 7 days, the spent medium was replaced with 10 ml of NLN-6.5S in each plate or the spent medium was diluted to obtain a sucrose concentration 6.5% in each plate. If the selectable marker gene was the NPTII gene, NAA, BAP and G418 were added to the medium. If the selectable marker gene was GAT, glyphosate was added in the medium. In this medium containing 6.5% sucrose, the embryos were cultured under dim light of approximately 240 foot-candles or 2,583 lux. The final concentration of G418 was 10 mg/l. and the concentration of glyphosate was 0.1 mM or 0.2 mM. A doubling agent was optionally added to the medium. Resistant embryos were recorded after two to three weeks of culture.

PHP18644 and GAT (glyphosate acetyltransferase) constructs (see Table 9) were used in transformation experiments using pre-incubated microspores. The GAT gene was isolated from a bacterium as described by Castle et al. (2004) Science 304: 1151-1154. The gene was shuffled 11 rounds for increasing expression level of glyphosate acetyltransferase. There was one to several variants in each shuffling round. PHP18644 also contains the GUS marker gene. The constructs are described in Table 9.

TABLE 9

Constructs

| Constructs | Promoter | Selectable Marker | Variants and rounds |
|---|---|---|---|
| PHP18644 | CaMV | NPT11 | NA |
| PHP22024 | H2b | GAT | GAT4604, R 8 |
| PHP21965 | SCP1 | GAT | GAT4604, R 8 |
| PHP22021 | H2b | GAT | GAT4618, R 11 |
| PHP23560 | SCP1 | GAT | GAT4621, R 11 |

For a detailed description of the protocol, see section labeled "Protocol" following the Examples.

Experiment 8

Development of a Selection Kill Curve Using Geneticin (G418) (Sigma G8168)

The objective was to determine the concentration of G418 that kills non-transgenic microspores.

Prior to this experiment, selection was done on solid medium, not in liquid medium. Using liquid selection for *Brassica* transgenic cells is novel. Selection in liquid medium is advantageous for at least the following reasons: (a) it allows selection at an early stage, thereby eliminating the need for subsequent transfers of explants, (b) it allows for a cleaner selection because the explants are generally smaller when they are in liquid medium and the liquid allows all the surfaces of the explant to be exposed to the selection agent, (c) it may reduce the frequency of chimeras, and (d) a lower amount of the selection agent is needed therefore reducing the toxicity to the researcher and the environment. The effect of various concentrations of kanamycin on embryo growth in liquid medium was tested. The result showed that 10 mg/l kanamycin was sufficient to bleach non-bombarded embryos and inhibit non-bombarded embryo growth. However, kanamycin at 10 and 20 mg/l failed to inhibit the growth of the bombarded embryos, although the embryos were pale green and purple in color. Accordingly, it was difficult to discriminate transgenic tissue or embryos from non-transgenic. Replacing kanamycin with 5-10 mg/l G418 in NLN with 6.5% sucrose medium, resulted in a cleaner selection. Table 10 shows that 5 to 10 mg/l G418 is sufficient to differentiate transformed cells from untransformed cells.

TABLE 10

Effect of G418 on embryo growth and survival

| Conc. Of G418 (mg/l) | # embryos | # Green embryos or with green island |
|---|---|---|
| 0 | 30 | 30 |
|  | 30 | 30 |
| 1.25 | 30 | 30 (paler) |
|  | 28 | 28 (paler) |
| 2.5 | 25 | 14 (light green, smaller size) |
|  | 25 | 11 (light green, smaller size) |
| 5 | 25 | 0 |
|  | 25 | 0 |
| 10 | 30 | 0 |
|  | 30 | 0 |

Experiment 9

Production of G418 and Glyphosate Resistant Tissue and Buds After Bombardment of Pre-Incubated Microspores Followed by Selection in Liquid Medium Containing G418 or Glyphosate The objective was to obtain transgenic plants by bombarding pre-incubated microspores that were cultured for up to 11 days and selecting resistant tissue and buds on liquid medium supplemented with 10 mg/l G418 or glyphosate at 0.1 mM and 0.2 mM.

In a first set of experiments, seven, eight, nine and eleven day old pre-incubated microspores were bombarded with PHP18644. NAA (0.5 mg/l) and BAP (0.05 mg/l), both growth regulators, were added to the selection medium comprising 10 mg/l G418 for enhanced cell growth conditions. Resistant microspores were transferred and cultured in the selection medium MMW+IAA+TDZ+AgNO$_3$5+C+K100 to induce resistant buds and confirm resistance. Accordingly, selection was initiated in the liquid culture medium with G418 and completed in the solid culture medium using kanamycin.

In a second set of experiments, 3, 4 and 5 day old pre-incubated microspores were bombarded with PHP23560. Glyphosate was added to the liquid and solid medium for selection.

Table 11 shows the results of the experiments. The data indicate that bombardment of pre-incubated microspores followed by selection in liquid medium using G418 or glyphosate produces resistant buds and PCR positive shoots.

TABLE 11

Effect of the pre-incubation period on resistant bud production

| Expt # | # days of culture | Embryos | Resistant buds (%) | PCR confirmed shoots |
|---|---|---|---|---|
| 1 | 9 | 2399 | 0 (0.0) | NA |
| 2 | 11 | 5629 | 0 (0.0) | NA |
| 3 | 8 | 1297 | 4 (0.3) | NA |
| 4 | 7 | 1998 | 4 (0.2) | NA |
| 5 | 5 | NA | NA | 6 |
| 6 | 4 | NA | NA | 3 |
| 7 | 3 | NA | NA | 3 |

Experiment 10

Determining the Effect of Osmotic Culture Medium After Bombardment on Resistant Embryo Production The objective was to determine whether culturing bombarded tissue on osmotic medium after bombardment would increase transformation efficiency.

Table 12 indicates that bombarded pre-incubated microspores cultured on osmotic medium for 4 hours after bombardment produced a greater number of transgenic sectors than bombarded pre-incubated microspores that were not cultured on osmotic medium soon after bombardment. After the osmotic treatment, the bombarded pre-incubated microspores were cultured on liquid NLN medium.

TABLE 12

Effect of osmotic culture after bombardment on resistant embryo production

| Treatments | # of embryos | # with green islands |
|---|---|---|
| Culture 0 hour after bombard | 2329 | 0 (0.0%) |
| Culture 4 hour after bombard | 5057 | 80 (1.6%) |

Experiment 11

Determining the Efficiency of Resistant Bud Production from Bombarded Pre-Incubated Microspores Selected on Liquid Medium Supplemented with G418 at 10 mg/l and Confirmation of Resistant Plants by PCR Analysis The objective was to confirm that selection in liquid medium produces resistant buds.

The construct used was PHP18644. Embryos that were resistant in the liquid selection medium were cultured in MMW+IAA (0.254 mg/l)+TDZ (1 mg/l)+AgNO3 (5 mg/l). Resistant buds were isolated and cultured in B5+GA+kanamycin (100 mg/l or MMW+kanamycin (100 mg/l) to produce shoots. Table 13 shows that resistant buds were regenerated from the embryos with sectors of resistance. Accordingly, selection in G418 liquid medium is efficient.

TABLE 13

G418 liquid medium selection efficiency in terms of resistant bud production.

| Rep # | # green embryos or islands | # embryos with resistant buds |
|---|---|---|
| Rep 1 | 51 | 40 |
| Rep 2 | 25 | 17 |
| Rep 3 | 1 | 1 |
| Rep 4 | 26 | 11 |

The nptll gene was confirmed in resistant plants using PCR analysis. Eight plants were selected at random and analyzed, six were found to have the nptll gene (Table 14).

TABLE 14

PCR analysis of resistant plants

| Reps | Resistant Plants | PCR-nptll positive |
|---|---|---|
| Rep 1 | 1 | 1 |
| Rep 2 | 1 | 1 |
| Rep 3 | 2 | 1 |
| Rep 4 | 4 | 3 |
| Total | 8 | 6 |

Experiment 12

Glyphosate Resistant Embryo Selection After Bombarding Pre-Incubated Microspores with PHP22021 and PHP22024 and Followed by Selection in Liquid Medium NLN-6.5S Containing 0.1 mM and 0.2 mM Glyphosate The objective was to compare the effect of glyphosate concentration on selection efficiency. Table 15 shows that using either 0.1 mM or 0.2 mM glyphosate allowed identification of resistant embryos. Both normal and abnormal embryos were produced. Although transgenics were identified using both 0.1 mM and 0.2 mM glyphosate, selection at 0.2 mM produced fewer false positive results. It was more efficient and eliminated additional transfers.

TABLE 15

Effect of the concentration of glyphosate on resistant embryo selection

| Plasmid | Rep # | Glyphosate | # plates | # embryos (normal)/plate | # embryos (abnormal)/plate |
|---|---|---|---|---|---|
| PHP22021 | 1 | 0.1 mM | 12 | 3 | 23.8 |
| PHP22021 | 2 | 0.1 mM | 6 | 1.1 | 1 |
|  |  | 0.2 mM | 6 | 0 | 0 |
| PHP22021 | 3 | 0.1 mM | 9 | 0.6 | 0.2 |
|  |  | 0.2 mM | 9 | 0.1 | 0 |
| PHP22024 | 4 | 0.1 mM | 8 | 9.8 | 8.4 |
|  |  | 0.2 mM | 8 | 0.9 | 1.4 |
| PHP22024 | 5 | 0.1 mM | 7 | 2.1 | 2.4 |
|  |  | 0.2 mM | 6 | 0 | 0 |
| PHP22024 | 6 | 0.1 mM | 8 | 3.4 | 5.9 |
|  |  | 0.2 mM | 8 | 1.5 | 3.9 |

Experiment 13

Determining the Effect of Sucrose Concentration in the Osmotic Medium on Resistant Embryo Production The purpose of this experiment was to find the optimal concentration of sucrose in the osmotic medium.

Microspores were cultured for 4-7 days using 17S/10S protocol. The construct used was PHP23560 and the concentration of DNA was 28 ng/preparation. The rupture disk was 900 psi. The bombarded microspores were cultured in the dark for 7-10 days in NLN-13S containing a doubling agent and 0.2 mM Glyphosate. The culture was diluted with NLN-OS without glyphosate to NLN-6.5S containing 0.1 mM glyphosate. The diluted cultures were incubated in the light for 2-3 weeks. There was no significant difference in the number of green embryos (normal and abnormal) produced using 15%, 17% and 19% sucrose.

The experiment was repeated as shown in Table 16. The results of this experiment showed that a sucrose concentration of 17% produced similar result as a sucrose concentration of 19% in four experiments.

TABLE 16

Effect of sucrose concentration in the osmotic medium on resistant embryo production

| Rep # | Sucrose concentration | # of plates | Resistant embryos/plate |
|---|---|---|---|
| 1 | 17% | 8 | 2.3 |
|  | 19% | 8 | 1.8 |
| 2 | 17% | 1 | 0 |
|  | 19% | 6 | 1 |
| 3 | 17% | 6 | 2.7 |
|  | 19% | 6 | 1.8 |
| 4 | 17% | 7 | 5.1 |
|  | 19% | 8 | 3.9 |
| Total | 17% |  | 2.5 |
|  | 19% |  | 2.1 |

Experiment 14

Determining the Effect of the Duration of the Osmotic Treatment on Resistant Embryo Production The objective was to determine whether a 4 hour or 20 hour culture in osmotic medium results in a greater number of transgenic events.

The construct used was PHP21965. Microspores were pre-incubated for 6 to 7 days, and then collected with 25 uM Nitex™ sieve. The collected microspores were subsequently loaded onto Nitex™ sieves with pore size of 20 uM. The bombarded microspores and Nitex™ sieves were cultured for 4 hours or 20 hours on osmotic medium B5+1 g/l MES+190 g/l sucrose+12 g/l gelrite (pH 5.8-6.0) after bombardments. Table 17 shows that treating microspores for 4 hours produced a comparable number of resistant embryos to treating microspores for 20 hours.

TABLE 17

Effect of the duration of the osmotic treatment on resistant embryo production

| Rep # | Osmotic duration | # bombardments | # resistant embyros |
|---|---|---|---|
| 1 | 4 h | 8 | 7 |
|   | 44 h | 4 | 1 |
| 2 | 4 h | 8 | 8 |
|   | 20 h | 8 | 11 |
| 3 | 4 h | 8 | 20 |
|   | 20 h | 8 | 4 |
| 4 | 4 h | 8 | 7 |
|   | 20 h | 8 | 10 |
| 5 | 4 h | 8 | 27 |
|   | 20 h | 8 | 40 |
| Summary | 4 h | 41 | 69 (1.7/bombardment) |
|   | 20 h (including 44 h) | 37 | 66 (1.8/bombardment) |

Experiment 15

Determining the Effect of the Rupture Disk Strength on Resistant Embryo Production The purpose of this experiment was to compare effect of 650 psi and 900 psi rupture disk strength on resistant embryo production. Construct PHP23560 was used for bombardments. A total of nine experiments were conducted to compare rupture disks of 650 psi and 900 psi strength. No significant difference was found between rupture disks of 650 psi and 900 psi strength (Table 18). The rupture disk 650 psi was easier to use than the 900 psi rupture disk because less time was needed to build up helium pressure.

TABLE 18

Effect of rupture disk strength on resistant embryo production

| Rep # | Rupture disks | # bombardments | # resistant embryos |
|---|---|---|---|
| 1 | 650 | 8 | 21 |
|   | 900 | 8 | 17 |
| 2 | 650 | 9 | 1 |
|   | 900 | 4 | 5 |
| 3 | 650 | 8 | 10 |
|   | 900 | 7 | 20 |
| 4 | 650 | 8 | 16 |
|   | 900 | 8 | 13 |
| 5 | 650 | 8 | 8 |
|   | 900 | 8 | 5 |
| 6 | 650 | 8 | 6 |
|   | 900 | 8 | 3 |
| 7 | 650 | 8 | 0 |
|   | 900 | 8 | 1 |
| 8 | 650 | 8 | 1 |
|   | 900 | 8 | 3 |
| 9 | 650 | 7 | 4 |
|   | 900 | 6 | 2 |
| Summary | 650 | 72 | 67 (0.93/bombardment) |
|   | 900 | 65 | 69 (1.06/bombardment) |

Experiment 16

PCR Analysis to Confirm Transgenic Plant Production via Bombarding Pre-Incubated Microspores One hundred twenty-five resistant plants were confirmed positive using PCR analysis in 33 transformation experiments. Each experiment, on average, produced 3.8 transgenic plants (Table 19). The data for PHP22024 and PHP22021 includes data produced using both the DNA expression cassette and the entire plasmid. For example, of the 13 experiments listed under PHP22024, 9 were done using the plasmid and 4 were done using the expression cassette. The number of GAT positive plants was 55 and 34 respectively.

TABLE 19

Results of the PCR analysis of resistant plants.

| Constructs | # Experiments | Plants analyzed | # GAT positive |
|---|---|---|---|
| PHP22024 | 13 | 89 | 89 |
| PHP21965 | 3 | 8 | 7 |
| PHP22021 | 17 | 31 | 29 |
| Total | 33 | 128 | 125 |

Experiment 17

Transgene Copy Number Analysis in GAT Transgenic Plants

Transgenic (T1) plants identified by glyphosate resistance were analyzed using Southern blot hybridization analysis. Plant genomic DNA was extracted using cetyltrimethylammonium bromide (CTAB) buffer (Rogers et al., (1994) *Plant Molecular Biology Manual*, $2^{nd}$ Ed. 1:1-8.). The DNA samples were digested with Bam HI or Pst I. The hybridization probe was the GAT gene. The hybridization was made following Rajasekaran et al. (2000) *Plant Cell Rep.* 19: 539-545. The GAT gene copy number was determined by the highest number of bands from the hybridization blots for each digest. For example, if only one band was produced from both Bam HI and Pst I blots for an event, it indicated that the event had one copy of the GAT gene. Results from 42 events showed 17 events or 40% had only one copy of the GAT gene (Table 20).

TABLE 20

Transgenic copy number analysis in GAT transgenic plants

| Constructs | Total number of events | Copy number of the GAT gene determined by Southern blot hybridization analysis | | | |
|---|---|---|---|---|---|
| | | 1 | 2 | 3 | >3 |
| PHP22021 | 11 | 8 | 1 | 0 | 2 |
| PHP22024 | 29 | 8 | 11 | 7 | 3 |
| PHP21965 | 2 | 1 | 1 | 0 | 0 |
| Total | 42 | 17 (40%) | 13 (31%) | 7 (17%) | 5 (12%) |

All publications and patent applications mentioned in the specification are indicative of the level of those skilled in the art to which this invention pertains and are incorporated by reference.

Although the foregoing invention has been described in some detail by way of illustration and example for purposes of clarity of understanding, it will be obvious that certain changes and modifications may be practiced within the scope of the appended claims.

Protocols
Production of Pre-Incubated Microspores

Microspores are cultured as is known to those skilled in the art, for example see Fukuoka et al. (1996) *Plant Physiol* 111:39-47; Keller et al. (1987) *Proc. 7th Int. Rapeseed Congr.* (Plant Breeding and Acclimatization Institute, Poznan, Poland) pp. 152-157, Swanson et al. (1987) *Plant Cell Reports* 6: 94-97 and Baillie et al. (1992) *Plant Cell Reports* 11: 234-237. A detailed procedure is provided as follows:

Collect about 400 buds at uni-nucleus microspore stage from a *Brassica* variety that is responsive to microspore culture and regeneration, for example 46A65, Westar or Topas. Sterilize the buds in 5% sodium hypochlorite solution (100% commercial bleach solution) and let sit for 15-20 minutes. Place the buds in sterile water for 5 minutes to rinse off bleach. Repeat this step two more times. Empty buds into blender cups and blend for 8 seconds at low speed in 20-25 ml B5-W. Filter contents through two nested 44 μm Nitex filters into 50 ml centrifuge tubes. Wash filters with 20-25 ml B5-W, cap tubes and centrifuge at about 1,000 revolutions per minute (rpm) for 6 minutes. Decant B5-W, add 45 ml B5-W, centrifuge, decant, add 45 ml B5-W, centrifuge and repeat for a total of 4 washes. Before plating microspores, adjust microspore density to 100,000 microspores per ml with NLN-17S using a heamocytometer. Plate microspore suspension in 9-cm plates at 6 ml/plate. Culture the plates (around 40) for 2-3 days at 31.5° C., followed by NLN-10S. Culture the plates at 25° C. for an additional 3-4 days.

Particle Bombardment

Methods of particle bombardment are known to those skilled in the art. Detailed directions and procedures are provided upon purchasing a particle gun. For example, see Manual of Biolistic PDS-1000/He Particle Delivery System. For additional references, see Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental. Methods, ed. Gamborg and Phillips (Springer-Verlag, Berlin); and McCabe et al. (1988) *Biotechnology* 6:923-926. A detailed procedure is provided below:

Make Gold Particle Aliquots

Use 250 mg gold particles with diameter of 0.6 micron. Add 1000 μl EtOH and sonicate 5-8 seconds. Divide gold suspension to two tubes (500 μl each) (Fisher 05-541-27). Centrifuge for one minute, 13,000 rpm and pipette off EtOH. Wash with 1 ml sterile distilled water three times. Wash gold pellets with 1000 μl EtOH and Pipette off EtOH. Add 800 μl EtOH to each tube and suspend gold particles. Weigh 16 tubes (Fisher 05-541-27). Aliquot 100 μl gold suspension to each tube. Centrifuge 30 seconds and pipette off EtOH. Dry for one hour and weigh tube/gold to calculate gold weight in each tube. Add sterile water to each tube to make gold concentration to 3 mg/50 μl. Suspend gold particles with pipette sucking-releasing and sonication (3 seconds). Aliquot gold suspension to new 1.5 ml tubes at 50 ul/tube (3 mg/tube). Store in −20 C. freezer.

Coat DNA on Gold Particles

Gold particle amount per shot is 100 μg/shot (3 mg/30 shots). Add 3 μg DNA/bp/prep plasmid DNA, 50 μl CaCl2 (2.5 M, aliquoted into small volumes), 20 μl spermidine (0.1 M, base-free, aliquoted into small volumes) to a tube of gold particle aliquot. Pipette 30-50 times after each addition. Shake for 3 minutes on vortex shaker. Centrifuge for 10 seconds at 10,000 rpm and discard supernatant. Gently add 200 μl 100% EtOH and set in ice for 10 minutes and discard supernatant. Wash gently with 200 μl 100% EtOH twice and discard washes. Add 150 μl 100% EtOH. Use 10 μl pipette tip to suspend the gold pellet. Fully suspend gold particles. Sonicate for 3 one-second dips to break small pellets. Sterilize macro-carrier discs in 70% EtOH for minimum 10 minutes. Transfer to 100% EtOH then dry in laminar flow cabinet. Place 5 μl DNA-coated gold particle suspension on the centre of each sterilized macro-carrier disc and dry for at least half an hour.

Biolistic Gun Operation

The microcarrier launch assembly parts, the macrocarrier holders, the rupture retaining cap, macroccarrier, petri dish holder and the stopping screens can be sterilized either by soaking (or spraying) in 70% EtOH for 15 minutes and drying in the laminar flow cabinet, or by autoclaving. The rupture disks should be sterilized in 50% iso-propanol for 10-30 seconds. Sterilize the chamber by spraying 70% EtOH. Build up helium pressure higher than rupture disk. Load the rupture disk retaining cap and microcarrier launch assembly and assemble in chamber. Place the microcarrier launch assembly in the first slot from the top. Position the sample on the petri dish holder at the third slot. Close the chamber. Set the vacuum switch on the gun to VAC position. Once the vacuum level is reached to or beyond 27 inch Hg, place the vacuum switch in the HOLD position. Press and hold FIRE switch until burst. Release the fire switch immediately and switch the VACUUM to the VENT position. After the vacuum is released, take out sample and microcarrier launch assembly. Repeat until all samples are bombarded.

Bombardment and Selection of Pre-Incubated Microspores

Culture microspores for 6-8 days using NLN-17S/10S protocol. Collect microspores with Nitex nylon sieve with 25 μm in pore size. Transfer microspores to a piece of Nitex nylon sieve and blot extra medium with filter papers. Transfer microspores and the Nitex to osmotic medium (B5+17% sucrose+1 g/l MES+0.8% gelrite, pH: 6.0) and treat at least one hour. Bombard samples with rupture disk 650 psi or 900 psi. Leave samples in the osmotic medium for at least 4 hours. Transfer microspores and Nitex to NLN-13S. A chromosome doubling agent can be added. Medium contains no selection agent (nptll selection) or 0.1-0.2 mM glyphosate (GAT selection). Each plate (9 cm) contains 5 ml medium and one piece of microspores/Nitex. Culture the bombarded microspores for 7 days at 25 C. in dark. Replace medium with 10 ml of NLN-6.5S with final concentration of NAA0.5BAP0.05+G418 (10 mg/l) if using the nptll gene as selectable marker or add 5 ml of NLN-OS with Glyphosate 0.1-0.2 mM if using the gat gene as selectable marker. Culture under light for 2 weeks.

Plant Regeneration

Culture green embryos or tissue in MMW+IAA2+TDZ0.5+STS6 with 25 mg/l kanamycin or 0.1 mM glyphosate for 4 weeks (STS6 is silver thiosulfate at concentration of 6 μM). Isolate regenerated buds and culture in MMW+BAP0.2 or B5+GA with 50 mg/l kanamycin or 0.1 mM glyphosate. Excise shoots and transfer to rooting medium ½ MMW+1%sucrose+IBA2 with 25 mg/l kanamycin or B5+GA with 0.1 mM glyphosate.

Transfer Resistant Plants to Soil and PCR Assay

Transfer resistant plants to soil in 36-cell flats after root is well developed. To maintain humidity, place lid on top for one week or until shoots have established themselves in soil. Assay for transgenics by PCR analysis using a PCR kit from Sigma (REDExtract-N-Amp Plant PCR kit). Transgenic plants must be labeled as "transgenic" or "GMO".

GUS Assay

GUS analysis is known to those skilled in the art. The protocol can be found in numerous references, for example Wu H, McCormac A C, Elliott M C, Chen D F (1998) *Agrobacterium*-mediated stable transformation of cell suspension cultures of barley (*Hordeum vulgare*). *Plant Cell Tissue and Organ Culture* 54:161-171.

PCR Analysis of the GAT and NPTII Genes

PCR analysis is known to those skilled in the art. The protocol can be found in numerous references. For example, PCR analysis of the nptII gene was done according to Broothaerts W, Wiersma P A, Lane W D (2001) Multiplex PCR combining transgene and S-allele control primers to simultaneously confirm cultivar identity and transformation in apple. *Plant Cell Rep* 20:349-353.

Plant DNA was extracted following Sigma™ Technical Bulletin Code MB-850 and using REDExtract-N-Amp™ Plant PCR kit. The temperature cycle was 95° C., 2 min; (94° C., 30 s; 64° C., 30 s; 72° C., 30 s) for 35 cycles; 75° C., 5' for the GAT gene amplification, or 95° C., 2 min; (95° C., 15 s; 60° C., 30 s; 72° C., 30 s) for 35 cycles; 75° C., 5' for the nptll gene.

Product Size

GAT4604 and 4618: 317 bp; GAT4621: 255 bp; NPTII: 700 bp.

| Reagents | Volume |
|---|---|
| Water | 5.2 μl |
| REDExtract-N-Amp PCR reaction mix | 10 μl |
| Primer-F (10 pM/μl) | 0.4 μl |
| Primer-R (10 pM/μl) | 0.4 μl |
| Leaf disk extract | 4 μl |
| Total volume | 20 μl |

Southern Blot Hybridization Analysis

Southern blot hybridization analysis is known to those skilled in the art. See for example, (see Rajasekarran et al. (2002) *Plant Cell Rep.* 19:539-545.

MEDIA RECIPES

MMW
MS salts and organics (Murashige and Skoog 1962 *Physiol. Plant.* 15:473-479)
Sucrose (3%)
MES (2 g/l)
Sigma agar #1296 (0.6%) pH 5.8
MMW+IAA+TDZ+AgNO3+Gly
MMW
IAA (2 mg/l)
TDZ (0.5 mg/l)
silver nitrate (5 mg/l)
glyphosate (0.1 mM)
MMW+BAP+Kan 25-50
MMW
BAP (4 mg/l)
Kanamycin (25-50 mg/l)
MMW+kan 50-100
MMW
Kanamycin (50-100 mg/l)
B5
B5 vitamins and minerals (Gamborg et al. (1968) *Exp. Cell Res.* 50:151-158)
Sucrose (2%)
Sigma agar (0.6%)
pH 5.8
B5+GA+Gly
B5
GA3 (0.1 mg/l)
Glyphosate (0.1 mM)
B5-W
B5 (no agar)
Sucrose (130 g/l)
NLN
Components are as Lichter (1982) *Z Pflanzenphysiol* 105: 427-434 without potato broth and plant growth regulators. Medium pH is 6.0.
NLN-17S, NLN-10S, NLN-6.5S
NLN contains 17%, 10% or 6.5% sucrose
Osmotic Medium for Pre-Incubated Microspores
B5
Sucrose 170 g/l
MES (1 g/l)
Phytagel (8-16 g/l)
pH: 6.0
Rooting Medium (½ MMW+1% sucrose+2 IBA)
Half strength MMW
Sucrose (10 g/l)
IBA (2 mg/lI)
*Trade-mark

REFERENCES CITED

Ahmen et al., (2000) WO0001223.
Albertsen et al. (1999) U.S. Pat. No. 5,962,769
Allison et al., (1986) *Virology* 154: 9-20
Baillie et al., (1992) *Plant Cell Reports* 11: 234-237
Baim et al. (1991) *Proc Natl. Acad. Sci. USA* 88:5072-5076
Ballas et al., (1989) *Nucleic Acids Res.* 17: 7891-7903
Barkley et al. (1980) in The Operon, pp. 177-220
Block and Debrouwer (1993) *Planta* 189: 218-225
Beck et al., (1982) *Gene* 19: 327-336
Beetham et al., (1999) *Proc. Natl. Acad. Sci. USA* 96: 8774-8778
Bidney et al., U.S. Pat. No. 5,932,782
Bonon (1993) Ph.D. Thesis University of Heidelberg Brown et al. (1987) *Cell* 49: 603-612
Campbell and Gowri (1990) *Plant Physiol.* 92: 1-11
Canevascini et al., (1996) *Plant Physiol* 112(2): 513-524
Castle et al., (2004) *Science* 304: 115101154
Chalfie et al. (1994) *Science* 263: 802-805.
Chamberland et al., (1992) *Plant Mol. Biol.* 19: 937-949
Chandrasekharan et al., (2003) *Plant J.* 33: 853-866
Chen and Beversdorf (1994) *Theoret. Appl. Genet.* 88:187-192
Christensen et al., (1989) *Plant Mol. Biol.* 12: 619-25 632
Christensen et al., (1992) *Plant Mol. Biol.* 18: 675-689
Christopherson et al., (1992) *Proc. Natl. Acad. Sci.* USA 89: 6314-6318
Chye and Zhao (2003) US 20030097682
Degenkolb et al., (1991) *Antimicrob. Agents Chemother.* 35: 1591-1595
Della-Cioppa et al. (1987) *Plant Physiol.* 84: 965-968
Deuschle et al., (1989) *Proc. Natl. Acad. Sci.* USA 86: 5400-5404
Deuschle et al., (1990) *Science* 248: 480-483
Elroy-Stein et al. (1989) *Proc. Natl. Acad. Sci.* USA 86: 6126-6130)
Figge et al., (1988) *Cell* 52: 713-722
Fuerst et al., (1989) *Proc. Natl. Acad. Sci.* USA 86: 2549-2553
Fukuoka et al., (1996) *Plant Physiol.* 111: 39-47
Fukuoka et al., (1998) *Plant Cell Reports* 17: 323-328
Gallie et al., (1989) in Molecular Biology of RNA, ed. Cech (Liss, N.Y.), pp. 237-256
Geiser et al., (1986) *Gene* 48: 109
Gill et al., (1988) *Nature* 334: 721-724
Gossen et al., (1992) *Proc. Natl Acad. Sci.* USA 89: 5547-5551
Gossen (1993) Ph.D. Thesis, University of Heidelberg
Guerineau et al., (1991) *Mol. Gen. Genet* 262: 141-144
Guevara-Garcia et al., (1993) *Plant J.* 4(3): 495-505
Hanson et al., (1997) *Mol. Gen Genet.* 254(3): 337-343
Hillenand-Wissman (1989) *Topics Mol. Struc. Biol.* 10: 143-162
Hlavka et al., (1985) Handbook of Experimental Pharmacology, Vol. 78 (Springer-Verlag, Berlin)
Hu et al., (1987) *Cell* 48: 555-566
Jefferson et al. (1986) *Proc. Natl. Acad. Sci.* USA 83: 8447-8451
Jefferson et al. (1987) *EMBO J.* 6: 3901-3907
Jobling et al. (1987) *Nature* 325: 622-625
Jones et al., (1994) *Science* 266: 789
Joshi et al. (1987) *Nucleic Acid Res.* 15: 9627-9639
Kawamata et al., (1997) *Plant Cell Physiol.* 38(7): 792-803
Keller et al. (1987) *Proc. 7th Int. Rapeseed Congr.* (Plant Breeding and Acclimatization Institute, Poznan, Poland) pp. 152-157
Kirihara et al., (1988) *Gene* 71: 359
Kleinschnidt et al., (1988) *Biochemistry* 27: 1094-1104
Labow et al. (1990) *Mol. Cell. Biol.* 10: 3343-3356
Lam (1994) *Results Probl. Cell Differ.* 20:181-196
Last et al., (1991) *Theor. Appl. Genet* 81: 581-588
Lilley et al., (1989) *Proceedings of the World Congress on Vegetable Protein Utilization in Human Foods and Animal Feedstuffs*, ed. Applewhite (American Oil Chemists Society, Champaign, Ill.), pp. 497-502
Lommel et al., (1991) *Virology* 81: 382-385
Macejak et al., (1991) *Nature* 353: 90-94
Maraschin et al., 2005 *J Exp Bot* 56: 1711-1726
Martin et al., (1993) *Science* 262: 1432
Matsuoka et al., (1993) *Proc Natl. Acad. Sci.* USA 90(20: 9586-9590
Mazodier et al., (1985) *Nucleic Acids Res.* 13: 195-205
McCabe et al., (1998) *Biotechnology* 6: 923-926
McElroy et al., (1990) *Plant Cell* 2: 163-171
Mindrinos et al., (1994) *Cell* 78: 1089
Mogen et al., (1990) *Plant Cell* 2:1261-1272
Moloney et al., (1989) *Plant Cell Reports* 8:238-242
Munroe et al., (1990) *Gene* 91: 151-158
Murray et al., (1989) *Nucleic Acid Res.* 17: 477-498
Musumura et al., (1989) *Plant Mol. Biol.* 12: 123
Nehlin et al., (2000) *Plant Physiol. Vol* 156: 175-183.
Odell et al., (1985) *Nature* 313: 810-812
Oliva et al., (1992) *Antimicrob. Agents Chemother.* 36: 913-919
Orozco et al., (1993) *Plant Mol. Biol.* 23(6): 1129-1138
Pedersen et al., (1986) *J. Biol. Chem.* 261: 6279
Prem et al., 2005 *In Vitro Cell. Dev. Biol.*—Plant 41: 266-273
Proudfoot (1991) *Cell* 64: 671-674
Radke et al., (1992) *Plant Cell Reports* 11: 499-505
Rajasekarran et al. (2002) *Plant Cell Reports* 19:539-545
Rasco-Gaunt et al., (2003) *Plant Cell Rep.* 21: 569-576
Reines et al., (1993) *Proc. Natl. Acad. Sci.* USA 90: 1917-1921
Reznikoff (1992) *Mol. Microbiol.* 6: 2419-2422
Rinehart et al., (1996) *Plant Physiol.* 112(3): 1331-1341
Russell et al., (1997) *Transgenic Res.* 6(2): 157-168
Salmeron et al., (2003) U.S. Pat. No. 6,528,702
Sanfacon et al., (1991) *Genes Dev.* 5: 141-149
Sanford et al., U.S. Pat. No. 4,945,050
Schubert et al., (1988) *J. Bacteriol.* 170: 5837-5847
Stewart and Broadway (2005) U.S. Pat. No. 6,927,322
Swanson et al., (1987) *Plant Cell Reports* 6: 94-97
Swanson et al., (1989) *Theor Appl Genet* 78: 525-530
Thompson et al., (1989) *BioEssays* 10: 108
Tomes et al., U.S. Pat. No. 5,879,918
Tomes et al., U.S. Pat. No. 5,886,244
Tomes et al., (1995) "Direct DNA Transfer into Intact Plant Calls via Microprojectile Bombardment," in *Plant Cell, Tissue, and Organ Culture: Fundamental. Methods*, ed. Gamborg and Phillips (Springer-Verlag, Berlin)
Touraev (1996) *Sex Plant Reprod* 9: 209-215
Van Camp et al., (1996) *Plant Physiol.* 112(2): 525-535
Van Damme et al., (1994) *Plant Mol. Biol.* 24: 825
Velten et al., (1984) *EMBO J.* 3: 2723-2730
Williamson et al., (1987) *Bur. J. Biochem* 165: 99-106
Wyborski et al., (1991) *Nucleic Acid Res.* 19:4647-4653
Yamamoto et al., (1997) *Plant J.* 12(2):255-265
Yamamoto et al., (1994) *Plant Cell Physiol.* 35(5): 773-778
Yao et al., (1992) *Cell* 71: 63-72
Yarranton (1992) *Curr. Opin. Biotech.* 3: 506-511
Zambretti et al., (1992) *Proc. Natl. Acad. Sci.* USA 89: 3952-3956

What is claimed is:

1. A method for producing a stably transformed *Brassica* plant, comprising:
   (a) isolating a microspore from a donor *Brassica* plant;
   (b) culturing said isolated microspore for a period of about two to about ten days from the time of isolation to produce an isolated pre-incubated microspore;
   (c) prior to step (d), culturing under conditions of plasmolysis the isolated pre-incubated microspore;
   (d) introducing, under conditions of plasmolysis, a DNA construct by microprojectile bombardment into a pre-incubated microspore to produce a transformed pre-incubated microspore;
   (e) after step (d), culturing under conditions of plasmolysis the transformed pre-incubated microspore;

(f) culturing the transformed pre-incubated microspore in or on a liquid selection medium to produce an embryo or tissue; and (g) regenerating a stably transformed *Brassica* plant from the embryo or tissue.

2. The method of claim 1 wherein plasmolysis is performed by (a) culturing the pre-incubated microspore on osmotic medium prior to, during and after bombardment or (b) culturing the pre-incubated microspores on wetted filter paper prior to, during and after bombardment.

3. The method of claim 2 wherein the pre-incubated microspore is cultured on osmotic medium for about between half an hour and four hours prior to bombardment and for about between four hours and twenty hours after bombardment.

4. The method of claim 1 wherein the liquid selection medium comprises a selection agent against a gene encoded by the DNA construct.

5. The method of claim 4 wherein the selection agent is selected from the group consisting of kanamycin, G418 and glyphosate.

6. The method of claim 1, further comprising a step of orientating the pre-incubated microspore prior to bombardment so that a surface of the microspore is exposed during the bombardment.

7. The method of claim 1, further comprising the step of collecting a population of pre-incubated microspore such that the population is enriched for microspores which are viable and embryogenic prior to bombardment.

8. The method of claim 7 wherein the step of selectively collecting the pre-incubated microspore is selected from the group consisting of a filtration step and a step of Percoll® gradient centrifugation.

9. The method of claim 1, wherein in step (d), the microprojectile bombardment is conducted using bombardment factors comprising about 12.5 ng to 5 µg of said DNA construct, about 15 µg to 100 µg gold particles per shot at the size of 0.4 micron to 0.6 micron, about 2.5 M $CaCl_2$, and a 650 to 900 psi rupture disk.

10. The method of claim 1, wherein the step of regenerating a stably transformed plant comprises culturing the bombarded pre-incubated microspore on a first liquid selection medium for a first period of time, on a second liquid selection medium for a second period of time, and then transferring the selected embryo or tissue derived from the pre-incubated microspore to solid medium for a third period of time.

11. The method of claim 1 further comprising use of a chromosome doubling agent to produce a doubled haploid transgenic plan, wherein the use occurs before, after, or both before and after bombardment of the pre-incubated microspore.

12. The method of claim 11 wherein use of a chromosome doubling agent occurs after bombardment.

13. The method of claim 11 wherein use of a chromosome doubling agent occurs prior to bombardment.

* * * * *